US012630814B2

(12) United States Patent
Kim et al.

(10) Patent No.: US 12,630,814 B2
(45) Date of Patent: May 19, 2026

(54) GLUTAMATE-CYSTEINE LIGASE VARIANT AND METHOD FOR PRODUCING GLUTATHIONE USING SAME

(71) Applicant: CJ CHEILJEDANG CORPORATION, Seoul (KR)

(72) Inventors: Yeonsoo Kim, Seoul (KR); Cheol Woong Ha, Seoul (KR); Eun Bin Yang, Seoul (KR); Yeong Eun Im, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 408 days.

(21) Appl. No.: 18/039,210

(22) PCT Filed: Sep. 8, 2021

(86) PCT No.: PCT/KR2021/012176
§ 371 (c)(1),
(2) Date: May 26, 2023

(87) PCT Pub. No.: WO2022/145623
PCT Pub. Date: Jul. 7, 2022

(65) Prior Publication Data
US 2025/0327056 A1     Oct. 23, 2025

(30) Foreign Application Priority Data
Jan. 4, 2021     (KR) ........................ 10-2021-0000361

(51) Int. Cl.
*C12P 21/02* (2006.01)
*C12N 9/00* (2006.01)

(52) U.S. Cl.
CPC ............... *C12N 9/93* (2013.01); *C12P 21/02* (2013.01); *C12Y 603/02002* (2013.01)

(58) Field of Classification Search
CPC ...................................................... C12N 9/93
See application file for complete search history.

(56) References Cited

U.S. PATENT DOCUMENTS

2016/0326510 A1     11/2016     Sasahara et al.

FOREIGN PATENT DOCUMENTS

| CN | 101407768 | A | 4/2009 |
|---|---|---|---|
| CN | 102296033 | B | 8/2013 |
| JP | 2003159049 | A | 6/2003 |
| JP | 2020-530260 | A | 10/2020 |
| KR | 10-2002-0019564 | A | 3/2002 |
| KR | 10-2004-0058327 | A | 7/2004 |
| WO | 2015115612 | A1 | 8/2015 |

OTHER PUBLICATIONS

Biterova, E.I. & Barycki, J.J., "Mechanistic Details of Glutathione Biosynthesis Revealed by Crystal Structures of *Saccharomyces cerevisiae* Glutamate Cysteine Ligase", Journal of Biological Chemistry, 2009, vol. 284, No. 47, pp. 32700-32708.(Year 2009).*
GenBank Database, "glutamate-cysteine ligase catalytic subunit [Exaiptasia diaphana]", GenPept, Accession No. ACC86274.1, Aug. 1, 2008, 1 page.
Sunagawa et al., "Hyperthermic stress-induced increase in the expression of glutamate-cysteine ligase and glutathione levels in the symbiotic sea anemone *Aiptasia pallida*", Comparative Biochemistry and Physiology, Part B, vol. 151, 2008, pp. 133-138.
Extended European Search Report issued in corresponding European Patent Application No. 21915421.8, dated Sep. 9, 2025.
Wu et al., "Effects of GSH1 and GSH2 Gene Mutation on Glutathione Synthetases Activity of *Saccharomyces cerevisiae*," Protein J, 36: 270-277 (2017).
NCBI Reference Sequence: NP_012434.1; glutamate—cysteine ligase [*Saccharomyces cerevisiae*S288C] (Oct. 2, 2020).
Sipes et al., "The Role of Glutathione in the Toxicity of Xenobiotic Compounds: Metabolic Activation of 1,2-Dibromoethane by Glutathione," Adv Exp Med Biol., 197: 457-467 (1986).
Pearson et al., "Improved tools for biological sequence comparison," Proc. Natl. Acad. Sci. USA, 85(8): 2444-2448 (1988).
Devereux et al., "A comprehensive set of sequence analysis programs for the VAX," Nucleic Acids Research, 12(1):387-395 (1984).
Altschul et al., "Basic Local Alignment Search Tool," J. Mol. Biol, 215: 403-410 (1990).
Lee et al., "Development of Reusable Split URA3-Marked Knockout Vectors for *Saccharomyces cerevisiae*," J. Microbiol. Biotechnol., 16(6): 979-982 (2006).
International Search Report issued in corresponding International Patent Application No. PCT/KR2021/012176 dated Apr. 12, 2022.

* cited by examiner

*Primary Examiner* — Suzanne M Noakes
(74) *Attorney, Agent, or Firm* — Morgan, Lewis & Bockius LLP

(57)     ABSTRACT

The present disclosure relates to a glutamate-cysteine ligase variant and a method of producing glutathione using the same.

20 Claims, No Drawings
Specification includes a Sequence Listing.

SEQUENCE LISTING

<160> NUMBER OF SEQ ID NOS: 15

<210> SEQ ID NO 1
<211> LENGTH: 678
<212> TYPE: PRT
<213> ORGANISM: Saccharomyces cerevisiae

<400> SEQUENCE: 1

```
Met Gly Leu Leu Ala Leu Gly Thr Pro Leu Gln Trp Phe Glu Ser Arg
1               5                   10                  15

Thr Tyr Asn Glu His Ile Arg Asp Glu Gly Ile Glu Gln Leu Leu Tyr
            20                  25                  30

Ile Phe Gln Ala Ala Gly Lys Arg Asp Asn Asp Pro Leu Phe Trp Gly
        35                  40                  45

Asp Glu Leu Glu Tyr Met Val Val Asp Phe Asp Asp Lys Glu Arg Asn
    50                  55                  60
```

```
Ser Met Leu Asp Val Cys His Asp Lys Ile Leu Thr Glu Leu Asn Met
65                  70                  75                  80

Glu Asp Ser Ser Leu Cys Glu Ala Asn Asp Val Ser Phe His Pro Glu
                85                  90                  95

Tyr Gly Arg Tyr Met Leu Glu Ala Thr Pro Ala Ser Pro Tyr Leu Asn
            100                 105                 110

Tyr Val Gly Ser Tyr Val Glu Val Asn Met Gln Lys Arg Arg Ala Ile
            115                 120                 125

Ala Glu Tyr Lys Leu Ser Glu Tyr Ala Arg Gln Asp Ser Lys Asn Asn
    130                 135                 140

Leu His Val Gly Ser Arg Ser Val Pro Leu Thr Leu Thr Val Phe Pro
145                 150                 155                 160

Arg Met Gly Cys Pro Asp Phe Ile Asn Ile Lys Asp Pro Trp Asn His
                165                 170                 175

Lys Asn Ala Ala Ser Arg Ser Leu Phe Leu Pro Asp Glu Val Ile Asn
            180                 185                 190

Arg His Val Arg Phe Pro Asn Leu Thr Ala Ser Ile Arg Thr Arg Arg
            195                 200                 205

Gly Glu Lys Val Cys Met Asn Val Pro Met Tyr Lys Asp Ile Ala Thr
    210                 215                 220

Pro Glu Thr Asp Asp Ser Ile Tyr Asp Arg Asp Trp Phe Leu Pro Glu
225                 230                 235                 240

Asp Lys Glu Ala Lys Leu Ala Ser Lys Pro Gly Phe Ile Tyr Met Asp
            245                 250                 255

Ser Met Gly Phe Gly Met Gly Cys Ser Cys Leu Gln Val Thr Phe Gln
            260                 265                 270

Ala Pro Asn Ile Asn Lys Ala Arg Tyr Leu Tyr Asp Ala Leu Val Asn
            275                 280                 285

Phe Ala Pro Ile Met Leu Ala Phe Ser Ala Ala Ala Pro Ala Phe Lys
    290                 295                 300

Gly Trp Leu Ala Asp Gln Asp Val Arg Trp Asn Val Ile Ser Gly Ala
305                 310                 315                 320

Val Asp Asp Arg Thr Pro Lys Glu Arg Gly Val Ala Pro Leu Leu Pro
                325                 330                 335

Lys Tyr Asn Lys Asn Gly Phe Gly Gly Ile Ala Lys Asp Val Gln Asp
            340                 345                 350

Lys Val Leu Glu Ile Pro Lys Ser Arg Tyr Ser Ser Val Asp Leu Phe
            355                 360                 365

Leu Gly Gly Ser Lys Phe Phe Asn Arg Thr Tyr Asn Asp Thr Asn Val
    370                 375                 380

Pro Ile Asn Glu Lys Val Leu Gly Arg Leu Leu Glu Asn Asp Lys Ala
385                 390                 395                 400

Pro Leu Asp Tyr Asp Leu Ala Lys His Phe Ala His Leu Tyr Ile Arg
            405                 410                 415

Asp Pro Val Ser Thr Phe Glu Glu Leu Leu Asn Gln Asp Asn Lys Thr
            420                 425                 430

Ser Ser Asn His Phe Glu Asn Ile Gln Ser Thr Asn Trp Gln Thr Leu
    435                 440                 445

Arg Phe Lys Pro Pro Thr Gln Gln Ala Thr Pro Asp Lys Lys Asp Ser
    450                 455                 460

Pro Gly Trp Arg Val Glu Phe Arg Pro Phe Glu Val Gln Leu Leu Asp
465                 470                 475                 480
```

```
Phe Glu Asn Ala Ala Tyr Ser Val Leu Ile Tyr Leu Ile Val Asp Ser
                485                 490                 495

Ile Leu Thr Phe Ser Asp Asn Ile Asn Ala Tyr Ile His Met Ser Lys
        500                 505                 510

Val Trp Glu Asn Met Lys Ile Ala His His Arg Asp Ala Ile Leu Phe
        515                 520                 525

Glu Lys Phe His Trp Lys Lys Ser Phe Arg Asn Asp Thr Asp Val Glu
    530                 535                 540

Thr Glu Asp Tyr Ser Ile Ser Glu Ile Phe His Asn Pro Glu Asn Gly
545                 550                 555                 560

Ile Phe Pro Gln Phe Val Thr Pro Ile Leu Cys Gln Lys Gly Phe Val
                565                 570                 575

Thr Lys Asp Trp Lys Glu Leu Lys His Ser Ser Lys His Glu Arg Leu
        580                 585                 590

Tyr Tyr Tyr Leu Lys Leu Ile Ser Asp Arg Ala Ser Gly Glu Leu Pro
        595                 600                 605

Thr Thr Ala Lys Phe Phe Arg Asn Phe Val Leu Gln His Pro Asp Tyr
    610                 615                 620

Lys His Asp Ser Lys Ile Ser Lys Ser Ile Asn Tyr Asp Leu Leu Ser
625                 630                 635                 640

Thr Cys Asp Arg Leu Thr His Leu Asp Asp Ser Lys Gly Glu Leu Thr
                645                 650                 655

Ser Phe Leu Gly Ala Glu Ile Ala Glu Tyr Val Lys Lys Asn Lys Pro
                660                 665                 670

Ser Ile Glu Ser Lys Cys
        675
```

```
<210> SEQ ID NO 2
<211> LENGTH: 2037
<212> TYPE: DNA
<213> ORGANISM: Saccharomyces cerevisiae

<400> SEQUENCE: 2
atgggactct tagctttggg cacgcctttg cagtggtttg agtctaggac gtacaatgaa     60
cacataaggg atgaaggtat cgagcagttg ttgtatattt tccaagctgc tggtaaaaga    120
gacaatgacc ctcttttttg gggagacgag cttgagtaca tggttgtaga ttttgatgat    180
aaggagagaa attctatgct cgacgtttgc catgacaaga tactcactga gcttaatatg    240
gaggattcgt ccctttgtga ggctaacgat gtgagttttc accctgagta tggccggtat    300
atgttagagg caacaccagc ttctccatat ttgaattacg tgggtagtta cgttgaggtt    360
aacatgcaaa aaagacgtgc cattgcagaa tataagctat ctgaatatgc gagacaagat    420
agtaaaaata acttgcatgt gggctccagg tctgtccctt tgacgctgac tgtcttcccg    480
aggatgggat gccccgactt tattaacatt aaggatccgt ggaatcataa aaatgccgct    540
tccaggtctc tgtttttacc cgatgaagtc attaacagac atgtcaggtt tcctaacttg    600
acagcatcca tcaggaccag gcgtggtgaa aaagtttgca tgaatgttcc catgtataaa    660
gatatagcta ctccagaaac ggatgactcc atctacgatc gagattggtt tttaccagaa    720
gacaaagagg cgaaactggc ttccaaaccg ggtttcattt atatggattc catgggtttt    780
ggcatgggct gttcgtgctt acaagtgacc tttcaggcac ccaatatcaa caaggcacgt    840
tacctgtacg atgcattagt gaattttgca cctataatgc tagccttctc tgccgctgcg    900
cctgctttta aaggttggct agccgaccaa gatgttcgtt ggaatgtgat atctggtgcg    960
```

-continued

```
gtggacgacc gtactccgaa ggaaagaggt gttgcgccat tactacccaa atacaacaag    1020
aacggatttg gaggcattgc caaagacgta caagataaag tccttgaaat accaaagtca    1080
agatatagtt cggttgatct tttcttgggt gggtcgaaat ttttcaatag gacttataac    1140
gacacaaatg tacctattaa tgaaaaagta ttaggacgac tactagagaa tgataaggcg    1200
ccactggact atgatcttgc taaacatttt gcgcatctct acataagaga tccagtatct    1260
acattcgaag aactgttgaa tcaggacaac aaaacgtctt caaatcactt tgaaaacatc    1320
caaagtacaa attggcagac attacgtttt aaaccccca cacaacaagc aaccccggac    1380
aaaaaggatt ctcctggttg gagagtggaa ttcagaccat ttgaagtgca actattagat    1440
tttgagaacg ctgcgtattc cgtgctcata tacttgattg tcgatagcat tttgaccttt    1500
tccgataata ttaacgcata tattcatatg tccaaagtat gggaaaatat gaagatagcc    1560
catcacagag atgctatcct atttgaaaaa tttcattgga aaaaatcatt tcgcaacgac    1620
accgatgtgg aaactgaaga ttattctata agcgagattt tccataatcc agagaatggt    1680
atatttcctc aatttgttac gccaatccta tgccaaaaag ggtttgtaac caaagattgg    1740
aaagaattaa agcattcttc caaacacgag agactatact attatttaaa gctaatttct    1800
gatagagcaa gcggtgaatt gccaacaaca gcaaaattct ttagaaattt tgtactacaa    1860
catccagatt acaaacatga ttcaaaaatt tcaaagtcga tcaattatga tttgctttct    1920
acgtgtgata gacttaccca tttagacgat tcaaaaggtg aattgacatc cttttttagga    1980 gctgaaattg cagaatatgt aaaaaaaaat aagccttcaa tagaaagcaa atgttaa      2037
```

<210> SEQ ID NO 3
<211> LENGTH: 678
<212> TYPE: PRT
<213> ORGANISM: Artificial Sequence
<220> FEATURE:
<223> OTHER INFORMATION: GSH1_G653M

<400> SEQUENCE: 3

```
Met Gly Leu Leu Ala Leu Gly Thr Pro Leu Gln Trp Phe Glu Ser Arg
1               5                   10                  15

Thr Tyr Asn Glu His Ile Arg Asp Glu Gly Ile Glu Gln Leu Leu Tyr
            20                  25                  30

Ile Phe Gln Ala Ala Gly Lys Arg Asp Asn Asp Pro Leu Phe Trp Gly
        35                  40                  45

Asp Glu Leu Glu Tyr Met Val Val Asp Phe Asp Lys Glu Arg Asn
    50                  55                  60

Ser Met Leu Asp Val Cys His Asp Lys Ile Leu Thr Glu Leu Asn Met
65                  70                  75                  80

Glu Asp Ser Ser Leu Cys Glu Ala Asn Asp Val Ser Phe His Pro Glu
                85                  90                  95

Tyr Gly Arg Tyr Met Leu Glu Ala Thr Pro Ala Ser Pro Tyr Leu Asn
            100                 105                 110

Tyr Val Gly Ser Tyr Val Glu Val Asn Met Gln Lys Arg Arg Ala Ile
        115                 120                 125

Ala Glu Tyr Lys Leu Ser Glu Tyr Ala Arg Gln Asp Ser Lys Asn Asn
    130                 135                 140

Leu His Val Gly Ser Arg Ser Val Pro Leu Thr Leu Thr Val Phe Pro
145                 150                 155                 160

Arg Met Gly Cys Pro Asp Phe Ile Asn Ile Lys Asp Pro Trp Asn His
                165                 170                 175
```

-continued

```
Lys Asn Ala Ala Ser Arg Ser Leu Phe Leu Pro Asp Glu Val Ile Asn
            180                 185                 190

Arg His Val Arg Phe Pro Asn Leu Thr Ala Ser Ile Arg Thr Arg Arg
            195                 200                 205

Gly Glu Lys Val Cys Met Asn Val Pro Met Tyr Lys Asp Ile Ala Thr
    210                 215                 220

Pro Glu Thr Asp Asp Ser Ile Tyr Asp Arg Asp Trp Phe Leu Pro Glu
225                 230                 235                 240

Asp Lys Glu Ala Lys Leu Ala Ser Lys Pro Gly Phe Ile Tyr Met Asp
            245                 250                 255

Ser Met Gly Phe Gly Met Gly Cys Ser Cys Leu Gln Val Thr Phe Gln
            260                 265                 270

Ala Pro Asn Ile Asn Lys Ala Arg Tyr Leu Tyr Asp Ala Leu Val Asn
            275                 280                 285

Phe Ala Pro Ile Met Leu Ala Phe Ser Ala Ala Pro Ala Phe Lys
    290                 295                 300

Gly Trp Leu Ala Asp Gln Asp Val Arg Trp Asn Val Ile Ser Gly Ala
305                 310                 315                 320

Val Asp Asp Arg Thr Pro Lys Glu Arg Gly Val Ala Pro Leu Leu Pro
            325                 330                 335

Lys Tyr Asn Lys Asn Gly Phe Gly Gly Ile Ala Lys Asp Val Gln Asp
            340                 345                 350

Lys Val Leu Glu Ile Pro Lys Ser Arg Tyr Ser Ser Val Asp Leu Phe
            355                 360                 365

Leu Gly Gly Ser Lys Phe Phe Asn Arg Thr Tyr Asn Asp Thr Asn Val
    370                 375                 380

Pro Ile Asn Glu Lys Val Leu Gly Arg Leu Leu Glu Asn Asp Lys Ala
385                 390                 395                 400

Pro Leu Asp Tyr Asp Leu Ala Lys His Phe Ala His Leu Tyr Ile Arg
            405                 410                 415

Asp Pro Val Ser Thr Phe Glu Glu Leu Leu Asn Gln Asp Asn Lys Thr
            420                 425                 430

Ser Ser Asn His Phe Glu Asn Ile Gln Ser Thr Asn Trp Gln Thr Leu
            435                 440                 445

Arg Phe Lys Pro Pro Thr Gln Gln Ala Thr Pro Asp Lys Lys Asp Ser
    450                 455                 460

Pro Gly Trp Arg Val Glu Phe Arg Pro Phe Glu Val Gln Leu Leu Asp
465                 470                 475                 480

Phe Glu Asn Ala Ala Tyr Ser Val Leu Ile Tyr Leu Ile Val Asp Ser
            485                 490                 495

Ile Leu Thr Phe Ser Asp Asn Ile Asn Ala Tyr Ile His Met Ser Lys
            500                 505                 510

Val Trp Glu Asn Met Lys Ile Ala His His Arg Asp Ala Ile Leu Phe
            515                 520                 525

Glu Lys Phe His Trp Lys Lys Ser Phe Arg Asn Asp Thr Asp Val Glu
    530                 535                 540

Thr Glu Asp Tyr Ser Ile Ser Glu Ile Phe His Asn Pro Glu Asn Gly
545                 550                 555                 560

Ile Phe Pro Gln Phe Val Thr Pro Ile Leu Cys Gln Lys Gly Phe Val
            565                 570                 575

Thr Lys Asp Trp Lys Glu Leu Lys His Ser Ser Lys His Glu Arg Leu
            580                 585                 590

Tyr Tyr Tyr Leu Lys Leu Ile Ser Asp Arg Ala Ser Gly Glu Leu Pro
```

-continued

```
        595                600                605
```

Thr Thr Ala Lys Phe Phe Arg Asn Phe Val Leu Gln His Pro Asp Tyr
    610                615                620

Lys His Asp Ser Lys Ile Ser Lys Ser Ile Asn Tyr Asp Leu Leu Ser
625                630                635                640

Thr Cys Asp Arg Leu Thr His Leu Asp Asp Ser Lys Met Glu Leu Thr
                645                650                655

Ser Phe Leu Gly Ala Glu Ile Ala Glu Tyr Val Lys Lys Asn Lys Pro
                660                665                670

Ser Ile Glu Ser Lys Cys
        675

<210> SEQ ID NO 4
<211> LENGTH: 33
<212> TYPE: DNA
<213> ORGANISM: Artificial Sequence
<220> FEATURE:
<223> OTHER INFORMATION: F_BamHI_GSH1

<400> SEQUENCE: 4
ggtaggatcc atgggactct tagctttggg cac                                    33

<210> SEQ ID NO 5
<211> LENGTH: 25
<212> TYPE: DNA
<213> ORGANISM: Artificial Sequence
<220> FEATURE:
<223> OTHER INFORMATION: R_GSH1_G653M

<400> SEQUENCE: 5
gtcaattcca tttttgaatc gtcca                                             25

<210> SEQ ID NO 6
<211> LENGTH: 25
<212> TYPE: DNA
<213> ORGANISM: Artificial Sequence
<220> FEATURE:
<223> OTHER INFORMATION: F_GSH1_G653M

<400> SEQUENCE: 6
attcaaaaat ggaattgaca tcctt                                            25

<210> SEQ ID NO 7
<211> LENGTH: 35
<212> TYPE: DNA
<213> ORGANISM: Artificial Sequence
<220> FEATURE:
<223> OTHER INFORMATION: R_XhoI_GSH1

<400> SEQUENCE: 7
atgactcgag ttaacatttg ctttctattg aaggc                                 35

<210> SEQ ID NO 8
<211> LENGTH: 33
<212> TYPE: DNA
<213> ORGANISM: Artificial Sequence
<220> FEATURE:
<223> OTHER INFORMATION: F_SpeI_GSH1_DW

<400> SEQUENCE: 8
tagaactagt actccttta tttcggttgt gaa                                     33

<210> SEQ ID NO 9
```

```
<211> LENGTH: 35
<212> TYPE: DNA
<213> ORGANISM: Artificial Sequence
<220> FEATURE:
<223> OTHER INFORMATION: R_NcoI_GSH1_DW

<400> SEQUENCE: 9
gctgccatgg gaatagtgtg aaccgataac tgtgt                              35

<210> SEQ ID NO 10
<211> LENGTH: 27
<212> TYPE: DNA
<213> ORGANISM: Artificial Sequence
<220> FEATURE:
<223> OTHER INFORMATION: R_AL killer

<400> SEQUENCE: 10
gagcaatgaa cccaataacg aaatctt                                       27

<210> SEQ ID NO 11
<211> LENGTH: 24
<212> TYPE: DNA
<213> ORGANISM: Artificial Sequence
<220> FEATURE:
<223> OTHER INFORMATION: F_BR killer

<400> SEQUENCE: 11
cttgacgttc gttcgactga tgag                                          24

<210> SEQ ID NO 12
<211> LENGTH: 500
<212> TYPE: DNA
<213> ORGANISM: Artificial Sequence
<220> FEATURE:
<223> OTHER INFORMATION: S. cerevisiae CJ-5 promoter

<400> SEQUENCE: 12
ctcttgaatg gcgacagcct attgcctcag tgttccctca acaaccttgg tagttggagc    60
gcaattagcg tatcctgtac catactaatt cccctctgcc cctcgacggc tgccattagt   120
cagcatggcg cgcacgtgac tacaactgtg gctggaaacc ttttcgtcct ccccggtttt   180
tcagtgagcc gactctacta caatgctttt tcatttttca ctcagaaaaa cctgcaattt   240
tccaaattag tcatgctctg tgcctccctt gacaaaggac atcttccctg tttataaacg   300
gcggcttacc aaaagttgaa gcttgttctt gcttcttatg agtggagcaa tcgattatat   360
tgaatcgttg tgctggagta gttggatctt tccacgtggt ctcgagtcac ttgtagaagc   420
tgaaaaattg agcaggttta gtatagggct acattgtagg gtggtttaga gtatcgaaaa   480
tatacatata gaagaataaa                                              500

<210> SEQ ID NO 13
<211> LENGTH: 678
<212> TYPE: PRT
<213> ORGANISM: Artificial Sequence
<220> FEATURE:
<223> OTHER INFORMATION: GSH1_G653M+C86R

<400> SEQUENCE: 13

Met Gly Leu Leu Ala Leu Gly Thr Pro Leu Gln Trp Phe Glu Ser Arg
1               5                   10                  15

Thr Tyr Asn Glu His Ile Arg Asp Glu Gly Ile Glu Gln Leu Leu Tyr
            20                  25                  30

Ile Phe Gln Ala Ala Gly Lys Arg Asp Asn Asp Pro Leu Phe Trp Gly
```

-continued

```
              35                  40                  45

Asp Glu Leu Glu Tyr Met Val Val Asp Phe Asp Asp Lys Glu Arg Asn
    50                  55                  60

Ser Met Leu Asp Val Cys His Asp Lys Ile Leu Thr Glu Leu Asn Met
65                  70                  75                  80

Glu Asp Ser Ser Leu Arg Glu Ala Asn Asp Val Ser Phe His Pro Glu
                85                  90                  95

Tyr Gly Arg Tyr Met Leu Glu Ala Thr Pro Ala Ser Pro Tyr Leu Asn
                100                 105                 110

Tyr Val Gly Ser Tyr Val Glu Val Asn Met Gln Lys Arg Arg Ala Ile
                115                 120                 125

Ala Glu Tyr Lys Leu Ser Glu Tyr Ala Arg Gln Asp Ser Lys Asn Asn
    130                 135                 140

Leu His Val Gly Ser Arg Ser Val Pro Leu Thr Leu Thr Val Phe Pro
145                 150                 155                 160

Arg Met Gly Cys Pro Asp Phe Ile Asn Ile Lys Asp Pro Trp Asn His
                165                 170                 175

Lys Asn Ala Ala Ser Arg Ser Leu Phe Leu Pro Asp Glu Val Ile Asn
                180                 185                 190

Arg His Val Arg Phe Pro Asn Leu Thr Ala Ser Ile Arg Thr Arg Arg
                195                 200                 205

Gly Glu Lys Val Cys Met Asn Val Pro Met Tyr Lys Asp Ile Ala Thr
    210                 215                 220

Pro Glu Thr Asp Asp Ser Ile Tyr Asp Arg Asp Trp Phe Leu Pro Glu
225                 230                 235                 240

Asp Lys Glu Ala Lys Leu Ala Ser Lys Pro Gly Phe Ile Tyr Met Asp
                245                 250                 255

Ser Met Gly Phe Gly Met Gly Cys Ser Cys Leu Gln Val Thr Phe Gln
                260                 265                 270

Ala Pro Asn Ile Asn Lys Ala Arg Tyr Leu Tyr Asp Ala Leu Val Asn
    275                 280                 285

Phe Ala Pro Ile Met Leu Ala Phe Ser Ala Ala Ala Pro Ala Phe Lys
    290                 295                 300

Gly Trp Leu Ala Asp Gln Asp Val Arg Trp Asn Val Ile Ser Gly Ala
305                 310                 315                 320

Val Asp Asp Arg Thr Pro Lys Glu Arg Gly Val Ala Pro Leu Leu Pro
                325                 330                 335

Lys Tyr Asn Lys Asn Gly Phe Gly Gly Ile Ala Lys Asp Val Gln Asp
                340                 345                 350

Lys Val Leu Glu Ile Pro Lys Ser Arg Tyr Ser Ser Val Asp Leu Phe
                355                 360                 365

Leu Gly Gly Ser Lys Phe Phe Asn Arg Thr Tyr Asn Asp Thr Asn Val
    370                 375                 380

Pro Ile Asn Glu Lys Val Leu Gly Arg Leu Leu Glu Asn Asp Lys Ala
385                 390                 395                 400

Pro Leu Asp Tyr Asp Leu Ala Lys His Phe Ala His Leu Tyr Ile Arg
                405                 410                 415

Asp Pro Val Ser Thr Phe Glu Glu Leu Leu Asn Gln Asp Asn Lys Thr
                420                 425                 430

Ser Ser Asn His Phe Glu Asn Ile Gln Ser Thr Asn Trp Gln Thr Leu
    435                 440                 445

Arg Phe Lys Pro Pro Thr Gln Gln Ala Thr Pro Asp Lys Lys Asp Ser
    450                 455                 460
```

```
Pro Gly Trp Arg Val Glu Phe Arg Pro Phe Glu Val Gln Leu Leu Asp
465             470             475             480

Phe Glu Asn Ala Ala Tyr Ser Val Leu Ile Tyr Leu Ile Val Asp Ser
            485             490             495

Ile Leu Thr Phe Ser Asp Asn Ile Asn Ala Tyr Ile His Met Ser Lys
            500             505             510

Val Trp Glu Asn Met Lys Ile Ala His His Arg Asp Ala Ile Leu Phe
            515             520             525

Glu Lys Phe His Trp Lys Lys Ser Phe Arg Asn Asp Thr Asp Val Glu
        530             535             540

Thr Glu Asp Tyr Ser Ile Ser Glu Ile Phe His Asn Pro Glu Asn Gly
545             550             555             560

Ile Phe Pro Gln Phe Val Thr Pro Ile Leu Cys Gln Lys Gly Phe Val
            565             570             575

Thr Lys Asp Trp Lys Glu Leu Lys His Ser Ser Lys His Glu Arg Leu
            580             585             590

Tyr Tyr Tyr Leu Lys Leu Ile Ser Asp Arg Ala Ser Gly Glu Leu Pro
        595             600             605

Thr Thr Ala Lys Phe Phe Arg Asn Phe Val Leu Gln His Pro Asp Tyr
        610             615             620

Lys His Asp Ser Lys Ile Ser Lys Ser Ile Asn Tyr Asp Leu Leu Ser
625             630             635             640

Thr Cys Asp Arg Leu Thr His Leu Asp Asp Ser Lys Met Glu Leu Thr
            645             650             655

Ser Phe Leu Gly Ala Glu Ile Ala Glu Tyr Val Lys Lys Asn Lys Pro
            660             665             670

Ser Ile Glu Ser Lys Cys
            675

<210> SEQ ID NO 14
<211> LENGTH: 25
<212> TYPE: DNA
<213> ORGANISM: Artificial Sequence
<220> FEATURE:
<223> OTHER INFORMATION: R_GSH1_C86R

<400> SEQUENCE: 14
ttagcctccc taagggacga atcct                                          25

<210> SEQ ID NO 15
<211> LENGTH: 25
<212> TYPE: DNA
<213> ORGANISM: Artificial Sequence
<220> FEATURE:
<223> OTHER INFORMATION: F_GSH1_C86R

<400> SEQUENCE: 15
cgtcccttag ggaggctaac gatgt                                          25
```

GLUTAMATE-CYSTEINE LIGASE VARIANT AND METHOD FOR PRODUCING GLUTATHIONE USING SAME

A computer readable text file, entitled "105135-5063-US_Sequence_Listing_ST25.txt," created on or about Jun. 10, 2024, with a file size of 23,294 bytes contains the sequence listing for this application and is hereby incorporated by reference in its entirety.

BACKGROUND OF THE INVENTION

1. Field of the Invention

The present disclosure relates to a novel glutamate-cysteine ligase variant and a method of producing glutathione using the same.

2. Description of the Related Art

Glutathione (GSH) is an organic sulfur compound that is most commonly present in cells, and it is in the form of a tripeptide in which three amino acids of glycine, glutamate, and cysteine are combined.

In the body, glutathione exists in two forms: reduced glutathione (GSH) and oxidized glutathione (GSSG). Reduced glutathione (GSH), which exists in a relatively high percentage under general circumstances, is mainly distributed in the liver and skin cells of the human body and has important roles such as an antioxidant function of decomposing and removing oxygen radicals, a detoxification function of removing exogenous compounds such as toxic substances, a whitening function of inhibiting melanin pigment production, etc.

Since production of glutathione gradually decreases with aging, a reduction in the production of glutathione, which has important roles in antioxidant and detoxification functions, promotes accumulation of oxygen radicals, which is one of the main causes of aging, and therefore, an external supply of glutathione is needed (Sipes I G et al., The role of glutathione in the toxicity of xenobiotic compounds: metabolic activation of 1,2-dibromoethane by glutathione, Adv Exp Med Biol. 1986, 197:457-67).

With such a variety of functions, glutathione has attracted much attention as a material in various fields such as pharmaceuticals, health functional foods, cosmetics, etc., and is also used in preparing flavoring ingredients, foods, and feed additives. It is known that glutathione has a significant effect on increasing the flavor of raw materials and maintaining a rich flavor, and glutathione can be used as a kokumi flavor enhancer by being used alone or in combination with other substances. Usually, kokumi substances have a richer flavor than existing umami substances such as nucleic acids, MSG, etc., and are known to be produced by decomposition and aging of proteins.

However, despite the increasing demand for glutathione that may be used in various fields as described above, an enzymatic synthesis process has not yet been commercialized due to the high production cost, and the market is not significantly activated because considerable costs are required for industrial production of glutathione.

The present inventors found that a newly developed glutamate-cysteine ligase variant-introduced microorganism is able to produce glutathione with high yield, thereby completing the present disclosure.

SUMMARY OF THE INVENTION

An object of the present invention is to provide a glutamate-cysteine ligase variant, in which an amino acid corresponding to position 653 from the N-terminus of an amino acid sequence of SEQ ID NO: 1 is substituted with methionine in a protein having a glutamate-cysteine ligase activity.

Another object of the present invention is to provide a polynucleotide encoding the variant, and a vector including the same.

Still another object of the present invention is to provide a microorganism producing glutathione by including any one or more of the variant; the polynucleotide encoding the variant; and the vector including the polynucleotide.

Still another object of the present invention is to provide a method of producing glutathione, the method including the step of culturing the microorganism.

DETAILED DESCRIPTION OF THE PREFERRED EMBODIMENTS

The present disclosure will be described in detail as follows. Meanwhile, each description and embodiment disclosed in this disclosure may also be applied to other descriptions and embodiments. That is, all combinations of various elements disclosed in this disclosure fall within the scope of the present disclosure. Further, the scope of the present disclosure is not limited by the specific description described below.

Further, those skilled in the art will recognize, or be able to ascertain using no more than routine experimentation, many equivalents to the specific embodiments of the disclosure described herein. Further, these equivalents should be interpreted to fall within the present disclosure.

An aspect of the present disclosure may provide a glutamate-cysteine ligase variant including an amino acid substitution in a protein having a glutamate-cysteine ligase activity, wherein the substitution includes a substitution of methionine for an amino acid corresponding to position 653 from the N-terminus of SEQ ID NO: 1.

The variant may be a protein variant in which glycine which is an amino acid corresponding to position 653 from the N-terminus of the glutamate-cysteine ligase amino acid sequence of SEQ ID NO: 1 is substituted with methionine.

The "glutamate-cysteine ligase (GCL)" of the present disclosure is an enzyme also called "glutamate-cysteine ligase" or "gamma-glutamylcysteine synthetase (GCS)". The glutamate-cysteine ligase is known to catalyze the following reaction:

L-glutamate+L-cysteine+ATP→gamma-glutamyl cysteine+ADP+Pi

Further, the reaction catalyzed by the glutamate-cysteine ligase is known as a first step of glutathione synthesis.

In the present disclosure, the amino acid sequence of the glutamate-cysteine ligase is an amino acid sequence encoded by gsh1 gene, and may also be referred to as "GSH1 protein" or "glutamate-cysteine ligase". The amino acid sequence constituting the glutamate-cysteine ligase of the present disclosure may be obtained from GenBank of NCBI, which is a known database. The glutamate-cysteine ligase may be a protein including the amino acid sequence of SEQ ID NO: 1, or consisting essentially of the same, or consisting of the same, but is not limited thereto. For another example, the glutamate-cysteine ligase may be derived from *Saccharomyces cerevisiae*, and for still another example, the amino acid corresponding to position 653 in the amino acid sequence of SEQ ID NO: 1 of *Saccharomyces* may be glycine. However, the glutamate-cysteine ligase is not limited thereto, and may include any sequence without limitation, as long as it is a sequence having the same glutamate-cysteine ligase activity as the amino acid sequence.

For specific example, the glutamate-cysteine ligase of the present disclosure may be a protein including the amino acid sequence of SEQ ID NO: 1 or an amino acid sequence having 80%, 85%, 90%, 95%, 96%, 97%, 98%, or 99% or more homology or identity thereto. Further, it is apparent that proteins having amino acid sequences in which some sequences are deleted, modified, substituted, or added are also included within the scope of the protein which is a target of variation of the present disclosure as long as the amino acid sequences have such homology or identity and exhibit the efficacy corresponding to that of the above protein.

Further, as an example of the glutamate-cysteine ligase of the present disclosure, it was defined as a protein including the amino acid sequence of SEQ ID NO: 1, but does not exclude a meaningless sequence upstream or downstream of the amino acid sequence of SEQ ID NO: 1, a naturally occurring mutation, or a silent mutation thereof, and it is apparent to those skilled in the art that proteins are also included in the scope of the glutamate-cysteine ligase of the present disclosure as long as they have activity identical or corresponding to that of the protein consisting of the amino acid sequence of SEQ ID NO: 1.

That is, in the present disclosure, although the expression 'protein or polypeptide having an amino acid sequence described by a specific SEQ ID NO', 'protein or polypeptide including an amino acid sequence described by a specific SEQ ID NO' is used, it is obvious that any protein including an amino acid sequence in which some sequences are deleted, modified, substituted, or added may be used in the present disclosure as long as the protein or polypeptide has the activity identical or corresponding to that of the polypeptide consisting of the amino acid sequence of the corresponding SEQ ID NO.

As used herein, the term "variant" or "modified polypeptide" refers to a protein, in which one or more amino acids differ from those of the recited sequence in conservative substitution and/or modification, but the functions or properties of the protein are maintained. With respect to the objects of the present disclosure, the variant may be a glutamate-cysteine ligase variant, in which an amino acid corresponding to position 653 from the N-terminus of SEQ ID NO: 1 is substituted with methionine in the glutamate-cysteine ligase described above, or a modified polypeptide having the glutamate-cysteine ligase activity. With regard to the variant of the present disclosure, the "glutamate-cysteine ligase variant" may also be described as "(modified) polypeptide having the glutamate-cysteine ligase activity", or "GSH1 variant".

The variant differs from sequences which are identified by substitution, deletion, or addition of several amino acids. Such a variant may generally be identified by modifying one or more amino acids of the amino acid sequence of the protein and evaluating the properties of the modified protein. In other words, the ability of the variant may be increased, unchanged, or decreased, as compared to that of the native protein. Further, some variant may include a modified polypeptide in which one or more parts such as an N-terminal leader sequence or a transmembrane domain are removed. Other variants may include variants in which a part is removed from the N- and/or C-terminus of a mature protein. The term "variant" or "modified polypeptide" may be used interchangeably with terms, such as modification, modified protein, mutant, mutein, divergent, variant, etc., and the term is not limited as long as it is used as a meaning of modification.

With respect to the objects of the present disclosure, the variant may have the increased activity of the modified protein, as compared to the natural wild-type or unmodified protein, or may increase the production amount of glutathione, as compared to the protein before modification, or the natural wild-type polypeptide or unmodified polypeptide, but is not limited thereto.

As used herein, the term "conservative substitution" refers to substitution of an amino acid with another amino acid having similar structural and/or chemical properties. The variant may have, for example, one or more conservative substitutions while maintaining one or more biological activities. This amino acid substitution may generally occur based on similarity in polarity, electric charge, solubility, hydrophobicity, hydrophilicity, and/or amphipathic nature of residues.

For example, among the electrically charged amino acids, positively charged (basic) amino acids include arginine, lysine, and histidine, and negatively charged (acidic) amino acids include glutamic acid and aspartic acid; and amino acids having uncharged side chains include glycine, alanine, valine, leucine, isoleucine, methionine, phenylalanine, tryptophan, and proline, serine, threonine, cysteine, tyrosine, asparagine, and glutamine.

Further, the variant may include deletions or additions of amino acids that have minimal effect on the properties and secondary structure of the polypeptide. For example, a polypeptide may be conjugated to a signal (or leader) sequence of a protein N-terminus that is involved in the transfer of proteins co-translationally or post-translationally. Further, the polypeptide may also be conjugated to another sequence or linker to identify, purify, or synthesize the polypeptide.

In one embodiment, the variant may be a glutamate-cysteine ligase variant, in which the amino acid corresponding to position 653 from the N-terminus of the amino acid sequence of SEQ ID NO: 1 is substituted with methionine. In one embodiment, the variant may be a variant, in which glycine corresponding to position 653 in the amino acid sequence of SEQ ID NO: 1 is substituted with methionine, but is not limited thereto.

As used herein, the 'substitution with another amino acid' is not limited as long as the substituted amino acid differs from the amino acid before substitution. Meanwhile, in the present disclosure, when expressed as 'a specific amino acid is substituted', it is obvious that the amino acid is substituted with an amino acid different from the amino acid before substitution, even though it is not separately indicated that the amino acid is substituted with another amino acid. As used herein, the term "corresponding position" refers to an amino acid residue at a position listed in a protein or polypeptide, or an amino acid residue similar to, identical to, or homologous to a residue listed in a protein or polypeptide. As used herein, the term "corresponding region" generally refers to a similar or corresponding position in a related protein or a reference protein.

In the present disclosure, specific numbering may be used for amino acid residue positions in proteins used in the present disclosure. For example, by aligning a target protein to be compared with the polypeptide sequence of the protein of the present disclosure, it is possible to renumber the position corresponding to the amino acid residue position of the protein of the present disclosure.

The glutamate-cysteine ligase variant of the present disclosure, in which the amino acid corresponding to position 653 from the N-terminus of the amino acid sequence of SEQ ID NO: 1 is substituted with methionine, may be a protein in which the amino acid corresponding to position 653 of SEQ ID NO: 1 is substituted with methionine in the amino acid sequence of SEQ ID NO: 1 or an amino acid sequence having 80%, 85%, 90%, 95%, 96%, 97%, 98%, or 99% or more homology or identity thereto. Such a variant may be a variant having an amino acid sequence having 80%, 85%, 90%, 95%, 96%, 97%, 98%, or 99% or more homology or identity to SEQ ID NO: 1 and having less than 100% homology or identity to SEQ ID NO: 1, but is not limited thereto.

The glutamate-cysteine ligase variant of the present disclosure, in which the amino acid corresponding to position 653 from the N-terminus of the amino acid sequence of SEQ ID NO: 1 is substituted with methionine, may include an amino acid sequence of SEQ ID NO: 3. Specifically, it may consist essentially of the amino acid sequence of SEQ ID NO: 3, and more specifically, may consist of any one amino acid sequence of SEQ ID NO: 3, but is not limited thereto.

Further, the variant may include the amino acid sequence of SEQ ID NO: 3, or may include an amino acid sequence having 80% or more homology or identity to SEQ ID NO: 3, provided that the amino acid at position 653 in the amino acid sequence is fixed (i.e., in the amino acid sequence of the variant, the amino acid corresponding to position 653 of SEQ ID NO: 3 is the same as the amino acid at position 653 of SEQ ID NO: 3), but is not limited thereto.

Specifically, the variant of the present disclosure may include a polypeptide having SEQ ID NO: 3 or having at least 80%, 90%, 95%, 96%, 97%, 98%, or 99% homology or identity to the amino acid sequence of SEQ ID NO: 3. Further, it is apparent that variants having amino acid sequences in which some sequences are deleted, modified, substituted, or added, in addition to position 653, are also included in the scope of the present disclosure as long as the amino acid sequences have such homology or identity and exhibit the efficacy corresponding to that of the variant.

As used herein, the term "homology" or "identity" means relevance between two given amino acid sequences or base sequences and may be expressed as a percentage. The terms "homology" and "identity" may often be used interchangeably.

The sequence homology or identity of a conserved polynucleotide or polypeptide is determined by standard alignment algorithms, and the default gap penalty established by a program used may be used together. Substantially, homologous or identical sequences are generally capable of being hybridized with the entirety or at least 50%, 60%, 70%, 80% or 90% of the entire length under moderately or highly stringent conditions. It is apparent that hybridization also includes hybridization of a polynucleotide with a polynucleotide including a general codon or a codon in consideration of codon degeneracy.

Whether any two polynucleotide or polypeptide sequences have homology, similarity, or identity may be determined using known computer algorithms such as the "FASTA" program, for example, using default parameters as in Pearson et al. (1988) [Proc. Natl. Acad. Sci. USA 85]: 2444. Alternatively, it may be determined using Needleman-Wunsch algorithm (Needleman and Wunsch, 1970, J. Mol. Biol. 48: 443-453) as performed in the Needleman program of the EMBOSS package (EMBOSS: The European Molecular Biology Open Software Suite, Rice et al., 2000, Trends Genet. 16: 276-277) (version 5.0.0 or later) (including GCG program package ((Devereux, J., et al., Nucleic Acids Research 12: 387 (1984)), BLASTP, BLASTN, FASTA (Atschul, [S.][F.,][ET AL, J MOLEC BIOL 215]: 403 (1990); Guide to Huge Computers, Martin J. Bishop,

[ED.,] Academic Press, San Diego, 1994, and [CARILLO et al.](1988) SIAM J Applied Math 48: 1073). For example, BLAST of the National Center for Biotechnology Information or ClustalW may be used to determine the homology, similarity, or identity.

The homology, similarity, or identity of polynucleotides or polypeptides may be determined by comparing sequence information using, for example, a GAP computer program such as Needleman et al. (1970), J Mol Biol. 48:443, as announced in, for example, Smith and Waterman, Adv. Appl. Math (1981) 2:482. In summary, the GAP program may be defined as the value acquired by dividing the number of similarly aligned symbols (namely, nucleotides or amino acids) by the total number of symbols in the shorter of two sequences. The default parameters for the GAP program may include (1) a binary comparison matrix (including values of 1 for identity and 0 for non-identity) and a weighted comparison matrix of Gribskov et al. (1986) Nucl. Acids Res. 14: 6745 (or EDNAFULL (EMBOSS version of NCBI NUC4.4) substitution matrix) as disclosed in Schwartz and Dayhoff, eds., Atlas Of Protein Sequence And Structure, National Biomedical Research Foundation, pp. 353-358 (1979); (2) a penalty of 3.0 for each gap and an additional 0.10 penalty for each symbol in each gap (or gap opening penalty of 10, gap extension penalty of 0.5); and (3) no penalty for end gaps.

Additionally, whether any two polynucleotide or polypeptide sequences have homology, similarity, or identity may be determined by comparing these sequences via Southern hybridization experiments under defined stringent conditions, and the appropriate hybridization conditions to be defined may be within the scope of the technology and may be determined by a method well known to one of ordinary skill in the art (e.g., J. Sambrook et al., Molecular Cloning, A Laboratory Manual, 2nd Edition, Cold Spring Harbor Laboratory press, Cold Spring Harbor, New York, 1989; F. M. Ausubel et al., Current Protocols in Molecular Biology, John Wiley & Sons, Inc., New York).

The glutamate-cysteine ligase variant of the present disclosure, in which the amino acid corresponding to position 653 from the N-terminus of the amino acid sequence of SEQ ID NO: 1 is substituted with methionine, may further include a variation, in which the amino acid corresponding to position 86 from the N-terminus of the amino acid sequence of SEQ ID NO: 1 is substituted with another amino acid.

Specifically, the variant may include a variation, in which cysteine corresponding to position 86 is substituted with another amino acid, for example, with arginine.

For example, the variant may include an amino acid sequence of SEQ ID NO: 13, may consist essentially of the same, or may consist of the same, but is not limited thereto.

Another aspect of the present disclosure may provide a polynucleotide encoding the variant.

As used herein, the term "polynucleotide" is a DNA or RNA strand having a certain length or more as a polymer of nucleotides in which nucleotide monomers are connected in a long chain by covalent bonds.

A gene encoding the glutamate-cysteine ligase of the present disclosure may be gsh1 gene.

The gene may be derived from yeast. Specifically, it may be derived from the genus *Saccharomyces*, and more specifically, it may be derived from *Saccharomyces cerevisiae*. Specifically, the gene may include any gene without limitation, as long as it encodes the polypeptide having glutamate-cysteine ligase activity derived from *Saccharomyces cerevisiae*, and in one embodiment, the gene may be a gene encoding the amino acid sequence of SEQ ID NO: 1, and in one embodiment, the gene may include a nucleotide sequence of SEQ ID NO: 2, but is not limited thereto.

The polynucleotide encoding the protein variant of the present disclosure may include any polynucleotide without limitation, as long as it is a polynucleotide encoding the glutamate-cysteine ligase variant of the present disclosure and a polypeptide having the activity corresponding thereto.

In the polynucleotide encoding the glutamate-cysteine ligase of the present disclosure and encoding the variant thereof, various modifications may be made in the coding region as long as the amino acid sequence of the polypeptide is not changed, in consideration of codon degeneracy or codons preferred in organisms that are intended to express the polypeptide.

Specifically, the polynucleotide encoding the protein variant of the present disclosure may include any polynucleotide sequence without limitation as long as it is a polynucleotide sequence encoding the protein variant, in which the amino acid corresponding to position 653 in the amino acid sequence of SEQ ID NO: 1 is substituted with methionine. For example, the polynucleotide encoding the protein variant of the present disclosure may be a polynucleotide sequence encoding the protein variant of the present disclosure, specifically, the protein including the amino acid sequence of SEQ ID NO: 3, or a polypeptide having homology or identity thereto, but is not limited thereto. The homology or identity is the same as described above.

Further, the polynucleotide encoding the protein variant of the present disclosure may include a probe that may be prepared from a known gene sequence, for example, a sequence without limitation as long as it is a sequence that hybridizes with a complementary sequence to the entirety or a part of the polynucleotide sequence under stringent conditions to encode the protein variant in which the amino acid corresponding to position 653 in the amino acid sequence of SEQ ID NO: 1 is substituted with methionine.

The "stringent conditions" mean conditions that enable specific hybridization between polynucleotides. These conditions are specifically described in documents (e.g., J. Sambrook et al., 1989, supra). For example, the stringent conditions may include conditions under which polynucleotides having high homology or identity, for example, 40% or higher, specifically 90% or higher, more specifically 95% or higher, 95% or higher, 96% or higher, 97% or higher, 98% or higher, more specifically, 99% or higher homology or identity are hybridized with each other and polynucleotides having homology or identity lower than the above homology or identity are not hybridized with each other, or ordinary washing conditions of Southern hybridization, in which washing is performed once, specifically, two to three times at a salt concentration and temperature equivalent to 60° C., 1×SSC, 0.1% SDS, specifically 60° C., 0.1×SSC, 0.1% SDS, more specifically, 68° C., 0.1×SSC, 0.1% SDS.

Hybridization requires that two nucleic acids have complementary sequences, although mismatches between bases are allowed depending on the stringency of hybridization. The term "complementary" is used to describe the relation between nucleotide bases capable of being hybridized with each other. For example, with regard to DNA, adenine is complementary to thymine and cytosine is complementary to guanine. Therefore, the polynucleotide of the present disclosure may also include substantially similar nucleic acid sequences as well as isolated nucleic acid fragments that are complementary to the entire sequence.

Specifically, a polynucleotide having homology or identity may be detected using hybridization conditions including a hybridization step at a Tm value of 55° C. and the above-described conditions. Further, the Tm value may be 60° C., 63° C., or 65° C., but is not limited thereto, and may be appropriately adjusted by those skilled in the art according to the purpose.

The appropriate stringency to hybridize the polynucleotide depends on the length and degree of complementarity of the polynucleotide, and the variables are well known in the art (see Sambrook et al., 1989, supra, 9.50-9.51, 11.7-11.8).

Still another aspect of the present disclosure may provide a vector including the polynucleotide encoding the protein variant.

As used herein, the term "vector" refers to a DNA construct including a polynucleotide sequence encoding a polypeptide of interest operably linked to a suitable expression control region (or expression control sequence) so that the polypeptide of interest may be expressed in a suitable host. The expression control region may include a promoter capable of initiating transcription, any operator sequence for controlling the transcription, a sequence encoding a suitable mRNA ribosome binding site, and a sequence controlling termination of transcription and translation. The vector may be transformed into a suitable host cell and then replicated or function independently of the host genome, or may be integrated into the genome itself.

For example, a polynucleotide encoding a protein of interest in a chromosome may be replaced with a mutated polynucleotide through a vector for intracellular chromosome insertion. Insertion of the polynucleotide into the chromosome may be performed by any method known in the art, for example, homologous recombination, but is not limited thereto. The vector may further include a selection marker for identifying chromosome insertion. The selection marker is for selecting the cells transformed with vectors, i.e., for identifying the insertion of a nucleic acid molecule of interest, and markers that confer selectable phenotypes such as drug resistance, auxotrophy, resistance to cytotoxic agents, or expression of surface polypeptides may be used. In an environment treated with a selective agent, only cells expressing the selection marker survive or exhibit other phenotypic traits, and thus transformed cells may be selected.

The vector used in the present disclosure is not particularly limited, and any vector known in the art may be used. Yeast expression vectors include both integrative yeast plasmid (Ylp) and extrachromosomal plasmid vectors. The extrachromosomal plasmid vector may include an episomal yeast plasmid (YEp), a replicative yeast plasmid (YRp) and a yeast centromere plasmid (YCp). In addition, artificial yeast chromosomes (YACs) may also be used as vectors of the present disclosure. For specific example, the applicable vectors may include pESCHIS, pESC-LEU, pESC-TRP, pESC-URA, Gateway pYES-DEST52, pAO815, pGAPZ A, pGAPZ B, pGAPZ C, pGAPα A, pGAPα B, pGAPα C, pPIC3.5K, pPIC6 A, pPIC6 B, pPIC6 C, pPIC6α A, pPIC6α B, pPIC6α C, pPIC9K, pYC2/CT, pYD1 Yeast Display Vector, pYES2, pYES2/CT, pYES2/NT A, pYES2/NT B, pYES2/NT C, pYES2/CT, pYES2.1, pYES-DEST52, pTEF1/Zeo, pFLD1, PichiaPink™, p427-TEF, p417-CYC, pGAL-MF, p427-TEF, p417-CYC, PTEF-MF, pBY011, pSGP47, pSGP46, pSGP36, pSGP40, ZM552, pAG303GAL-ccdB, pAG414GAL-ccdB, pAS404, pBridge, pGAD-GH, pGAD T7, pGBK T7, pHIS-2, pOBD2, pRS408, pRS410, pRS418, pRS420, pRS428, yeast micron A form, pRS403, pRS404, pRS405, pRS406, pYJ403, pYJ404, pYJ405 and pYJ406, but are not limited thereto.

As used herein, the term "transformation" means that a vector including a polynucleotide encoding a target protein is introduced into a host cell or a microorganism so that the protein encoded by the polynucleotide may be expressed in the host cell. The transformed polynucleotide may be located by being inserted into the chromosome of the host cell or located outside the chromosome as long as it may be expressed in the host cell. Further, the polynucleotide includes DNA and RNA encoding a protein of interest. The polynucleotide may be introduced in any form as long as it may be introduced into a host cell and then expressed. For example, the polynucleotide may be introduced into a host cell in the form of an expression cassette, which is a gene construct containing all elements required for self-expression. The expression cassette may usually include a promoter operably linked to the polynucleotide, a transcription termination signal, a ribosome binding site, and a translation termination signal. The expression cassette may be in the form of an expression vector capable of self-replicating. Further, the polynucleotide may be introduced into a host cell in its own form and operably linked to a sequence required for expression in the host cell, but is not limited thereto.

Further, as used herein, the term "operably linked" means that the gene sequence is functionally linked to a promoter sequence that initiates and mediates transcription of the polynucleotide encoding the polypeptide of interest of the present disclosure.

The method of transforming the vector of the present disclosure includes any method of introducing a nucleic acid into a cell, and may be performed by selecting an appropriate standard technique, as known in the art, according to the host cell. For example, the method may include electroporation, calcium phosphate (CaPO4) precipitation, calcium chloride ($CaCl_2$) precipitation, microinjection, a polyethylene glycol (PEG) method, a DEAE-dextran method, a cationic liposome method, and a lithium acetate-DMSO method, etc., but is not limited thereto.

The present disclosure may provide a microorganism producing glutathione by including any one or more of the variant, the polynucleotide encoding the variant; and the vector including the polynucleotide.

As used herein, the term "microorganism" includes all wild-type microorganisms or naturally or artificially genetically modified microorganisms, and it is a concept including all of microorganisms in which a specific mechanism is weakened or strengthened due to insertion of a foreign gene or an activity enhancement or inactivation of an endogenous gene. In the present disclosure, the microorganism may include any microorganism without limitation as long as it is a microorganism in which the glutamate-cysteine ligase variant of the present disclosure is introduced or included.

The microorganism is, for example, a cell or microorganism that is transformed with a gene encoding a target protein or a vector including the same, and expresses the target protein. With respect to the objects of the present disclosure, the host cell or microorganism is any microorganism as long as it is able to produce glutathione by including the glutamate-cysteine ligase variant.

The "glutathione" of the present disclosure is used interchangeably with "GSH", and refers to a tripeptide consisting of three amino acids of glutamate, cysteine, and glycine. Glutathione may be used as a material in pharmaceuticals, health functional foods, flavoring ingredients, foods, feed additives, cosmetics, etc., but is not limited thereto.

In the present disclosure, the "microorganism producing glutathione" includes all microorganisms in which genetic variation occurs naturally or artificially, and is a microorganism in which a specific mechanism is weakened or strengthened due to insertion of a foreign gene or an activity enhancement or inactivation of an endogenous gene, and may be a microorganism in which genetic variations have occurred or activity has been enhanced for the production of desired glutathione. With respect to the objects of the present disclosure, the microorganism producing glutathione may refer to a microorganism that includes the glutamate-cysteine ligase to produce an excessive amount of the desired glutathione, as compared to a wild-type or unmodified microorganism. The "microorganism producing glutathione" may be used interchangeably with terms such as "glutathione-producing microorganism", "microorganism having glutathione-producing ability", "glutathione-producing strain", "strain having glutathione-producing ability, etc.

The type of the microorganism producing glutathione is not particularly limited, as long as the microorganism is able to produce glutathione, but it may be a microorganism of the genus *Saccharomyces*, specifically, *Saccharomyces cerevisiae*, but is not limited thereto.

The parent strain of the glutathione-producing microorganism including the variant is not particularly limited, as long as it is able to produce glutathione. The microorganism may further include variations such as enhancement of biosynthetic pathway for increasing glutathione-producing ability, release of feedback inhibition, inactivation of genes that weakens the decomposition pathway or biosynthetic pathway, not excluding naturally occurring variations. In one embodiment, the microorganism may include a variation that increases the glutathione-producing ability in the expression control region of the glutamate-cysteine ligase. The variation may be any one or more variations selected from $-250(C{\rightarrow}T)$, $-252(G{\rightarrow}A)$, $-398(A{\rightarrow}T)$, $-399(A{\rightarrow}C)$, $-407(T{\rightarrow}C)$ and $-409(T{\rightarrow}C)$ upstream of GSH1 ORF, but is not limited thereto.

The microorganism including any one or more of the variant of the present disclosure; the polynucleotide encoding the variant; and the vector including the polynucleotide may be a microorganism expressing the glutamate-cysteine ligase variant, in which the amino acid corresponding to position 653 in the amino acid sequence of SEQ ID NO: 1 is substituted with methionine, but is not limited thereto.

The glutamate-cysteine ligase and the variant thereof are as described above.

As used herein, the protein "to be expressed/expressed" means a state in which a target protein is introduced into a microorganism or modified to be expressed in a microorganism. When the target protein is a protein present in microorganisms, it means a state in which its activity is enhanced, as compared to the endogenous activity or activity before modification.

The microorganism expressing the protein variant of the present disclosure may be a microorganism modified to express the protein variant of the present disclosure, and therefore, still another aspect of the present disclosure provides a method of preparing the microorganism expressing the protein variant of the present disclosure.

In the present disclosure, "introduction of a protein" refers to exhibiting activity of a particular protein which is not originally possessed by a microorganism, or exhibiting enhanced activity, as compared to the intrinsic activity of the corresponding protein or the activity before modification. For example, the introduction of a protein may refer to introduction of a particular protein, introduction of a polynucleotide encoding a particular protein into a chromosome of the microorganism, or introduction of a vector including a polynucleotide encoding a particular protein into a microorganism, thereby expressing the activity thereof.

As used herein, the term "enhancement" of polypeptide or protein activity means that the activity of a polypeptide or protein is increased as compared to the intrinsic activity. The enhancement may be used interchangeably with terms such as up-regulation, overexpression, increase, etc. Here, the increase may include both exhibiting activity that was not originally possessed and exhibiting improved activity, as compared to the intrinsic activity or activity before modification. The "intrinsic activity" means activity of a specific polypeptide or protein originally possessed by a parent strain before change of the trait or an unmodified microorganism when the trait is changed by genetic variation due to natural or artificial factors. This may be used interchangeably with "activity before modification". The fact that the activity of a polypeptide or protein is "enhanced" or "increased", as compared to the intrinsic activity, means that the activity of the polypeptide or protein is improved, as compared to the activity of a specific polypeptide or protein originally possessed by a parent strain before change of the trait or an unmodified microorganism.

The "activity enhancement" may be achieved through the introduction of a foreign polypeptide or protein or the enhancement of intrinsic activity of the polypeptide or protein, specifically, through the enhancement of intrinsic activity of the polypeptide or protein. The enhancement of activity of the polypeptide or protein may be confirmed by an increase in the degree of activity and the expression level of the corresponding polypeptide or protein or in the amount of a product produced from the corresponding protein.

For the activity enhancement of the polypeptide or protein, various methods well known in the art may be applied, and the method is not limited as long as the activity of the polypeptide or protein of interest may be enhanced, as compared to that of the microorganism before being modified. Specifically, genetic engineering and/or protein engineering well known to those skilled in the art, which are routine methods of molecular biology, may be used, but the method is not limited thereto (Sitnicka et al. Functional Analysis of Genes. Advances in Cell Biology. 2010, Vol. 2. 1-16, Sambrook et al. Molecular Cloning 2012, etc.).

Specifically, the method of enhancing the activity of the polypeptide or protein using genetic engineering may be performed by, for example:

1) increase in the intracellular copy number of the gene or polynucleotide encoding the polypeptide or protein;
2) replacement of a gene expression regulatory region on a chromosome encoding the polypeptide or protein with a sequence exhibiting strong activity;
3) modification of a start codon of the polypeptide or protein or a base sequence encoding a 5'-UTR region;
4) modification of the polynucleotide sequence on the chromosome to enhance the activity of the polypeptide or protein;
5) introduction of a foreign polynucleotide exhibiting the activity of the polypeptide or protein or a codon-optimized variant of the polynucleotide; or
6) a combination of the above methods, but is not limited thereto.

The method of enhancing activity of the polypeptide or protein using the protein engineering method may be performed by, for example, modifying or chemically modifying an exposed region selected by analyzing a three-dimensional structure of the polypeptide or protein, without being limited thereto.

(1) The increase in the intracellular copy number of the gene or polynucleotide encoding the polypeptide or protein may be performed by any method well known in the art, e.g., by introducing a vector, which replicates and functions irrespective of a host cell and is operably linked to the gene or polynucleotide encoding the corresponding polypeptide or protein, into a host cell. Alternatively, it may be performed by introducing a vector, which is operably linked to the gene and is capable of inserting the gene or polynucleotide into the chromosome of the host cell, into the host cell, but is not limited thereto.

(2) The replacement of a gene expression regulatory region (or expression regulatory sequence) on a chromosome encoding the polypeptide or protein with a sequence exhibiting strong activity may be performed by any method known in the art, e.g., by inducing mutation in the sequence by deletion, insertion, non-conservative or conservative substitution of the nucleotide sequence, or any combination thereof or by replacing the sequence with a nucleotide sequence with stronger activity, to further enhance the activity of the expression regulatory region. The expression regulatory region may include, but is not particularly limited to, a promoter, an operator sequence, a ribosome-binding site-encoding sequence, and a sequence for regulating termination of transcription and translation. The method may be specifically performed by linking a stronger heterologous promoter instead of an intrinsic promoter, but is not limited thereto.

Examples of known promoters for eukaryotes include promoters for translation elongation factor 1 (TEF1), glycerol-3-phosphate dehydrogenase 1 (GPD1), 3-phosphoglycerate kinase or other glycolytic enzymes such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase, and examples of another yeast promoter which is an inducible promoter with additional advantage of transcription controlled by growth conditions include promoters for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization, and when the host cell is a yeast, available promoters may include TEF1 promoter, TEF2 promoter, GAL10 promoter, GAL1 promoter, ADH1 promoter, ADH2 promoter, PHO5 promoter, GAL1-10 promoter, TDH3 promoter (GPD promoter), TDH2 promoter, TDH1 promoter, PGK1 promoter, PYK2 promoter, ENO1 promoter, ENO2 promoter, and TP11 promoter, and vectors and promoters suitable for use in yeast expression are further described in EP 073657, but are not limited thereto. Yeast enhancers may also be advantageously used with the yeast promoters, but are not limited thereto.

(3) The modification of a start codon of the polypeptide or protein or a base sequence encoding a 5'-UTR region may be performed by any method known in the art, e.g., by substituting an intrinsic initiation codon of the polypeptide or protein with another initiation codon with a higher expression level of the polypeptide or protein, as compared to the intrinsic initiation, but is not limited thereto.

(4) The modification of the polynucleotide sequence on the chromosome to enhance the activity of the polypeptide or protein may be performed by any method known in the art, e.g., by inducing modification on an expression regulatory sequence by deletion, insertion, non-conservative or conservative substitution, or any combination thereof to further enhance the activity of the polynucleotide sequence or by replacing the sequence with a polynucleotide sequence modified to have stronger activity. The replacing may be specifically insertion of the gene into the chromosome by homologous recombination, but is not limited thereto.

A vector used herein may further include a selection marker to detect the chromosomal insertion. The selection marker is as described above.

(5) The introduction of a foreign polynucleotide exhibiting the activity of the polypeptide or protein may be performed by any method known in the art, e.g., by introducing a foreign polynucleotide encoding a polypeptide or protein having activity identical/similar to that of the polypeptide or protein, or by introducing a codon optimized variant polynucleotide thereof into a host cell. The origin or sequence of the foreign polynucleotide is not particularly limited as long as the foreign polynucleotide exhibits activity identical/similar to that of the polypeptide or protein. In addition, a polynucleotide codon-optimized for optimized transcription and translation of the introduced foreign polynucleotide in the host cell may be introduced into the host cell. The introduction may be performed by any known transformation method appropriately selected by those of ordinary skill in the art. As the introduced polynucleotide is expressed in the host cell, the polypeptide or protein is produced, thereby increasing the activity thereof.

Finally, (6) the combination of the above-described methods may be performed by applying one or more methods of (1) to (5) in combination.

The enhancement of the activity of the polypeptide or protein as described above may be an increase in the activity or concentration of the corresponding polypeptide or protein, as compared to the activity or concentration of the polypeptide or protein expressed in a wild-type or a microorganism before modification, or an increase in an amount of a product obtained from the corresponding polypeptide or protein, but is not limited thereto.

As used herein, the term "strain before modification" or "microorganism before modification" does not exclude strains including mutations naturally occurring in microorganisms and may refer to a wild-type strain or natural-type strain itself, or a strain before being transformed by genetic modification due to a natural or artificial factor. The "strain before modification" or "microorganism before modification" may be used interchangeably with "unmutated strain", "unmodified strain", "unmutated microorganism", "unmodified microorganism", or "reference microorganism".

As used herein, the microorganism including the glutamate-cysteine ligase variant, or including the polynucleotide encoding the same or the vector including the polynucleotide may be a recombinant microorganism, and the recombination may be achieved by genetical modification such as transformation.

For example, the microorganism may be a recombinant microorganism prepared by transformation using the vector including the polynucleotide, but is not limited thereto. The recombinant microorganism may be yeast, and an example thereof may be a microorganism of the genus *Saccharomyces*, specifically, *Saccharomyces cerevisiae*, but is not limited thereto.

Still another aspect of the present disclosure provides a method of producing glutathione, the method including the step of culturing the microorganism. The microorganism and glutathione are as described above.

As the medium and other culture conditions used for culturing the strain of the present disclosure, any medium may be used without particular limitation as long as it is a medium commonly used for culturing microorganisms of the genus *Saccharomyces*. Specifically, the strain of the present disclosure may be cultured in a common medium containing proper carbon sources, nitrogen sources, phosphorus sources, inorganic compounds, amino acids and/or vitamins, etc., while controlling the temperature, pH, etc., under aerobic or anaerobic conditions.

In the present disclosure, the carbon sources include carbohydrates such as glucose, fructose, sucrose, maltose, etc.; sugar alcohols such as mannitol, sorbitol, etc.; organic acids such as pyruvic acid, lactic acid, citric acid, etc.; amino acids such as glutamic acid, methionine, lysine, etc.; and the like, but are not limited thereto. Further, natural organic nutrients such as starch hydrolysate, molasses, blackstrap molasses, rice bran, cassava, sugarcane residue, and corn steep liquor may be used. Specifically, carbohydrates such as glucose and sterilized pretreated molasses (namely, molasses converted to reducing sugar) may be used, and appropriate amounts of other carbon sources may be used in various manners without limitation. These carbon sources may be used alone or in a combination of two or more thereof.

As the nitrogen sources, inorganic nitrogen sources such as ammonia, ammonium sulfate, ammonium chloride, ammonium acetate, ammonium phosphate, ammonium carbonate, ammonium nitrate, etc.; and organic nitrogen sources such as amino acids, peptone, NZ-amine, meat extract, yeast extract, malt extract, corn steep liquor, casein hydrolysate, fish or decomposition products thereof, and skim soybean cake or decomposition products thereof, etc. may be used. These nitrogen sources may be used alone or in a combination of two or more thereof, but are not limited thereto.

The phosphorus sources may include monopotassium phosphate, dipotassium phosphate, or sodium-containing salts corresponding thereto. As the inorganic compounds, sodium chloride, calcium chloride, iron chloride, magnesium sulfate, iron sulfate, manganese sulfate, calcium carbonate, etc. may be used.

In addition to these compounds, amino acids, vitamins and/or suitable precursors, etc. may be contained. Specifically, L-amino acids, etc. may be added to the culture medium for the strain. Specifically, glycine, glutamate, and/or cysteine, etc. may be added, and if necessary, L-amino acids such as lysine, etc. may be further added, but is not necessarily limited thereto.

These mediums or precursors may be added to the culture batchwise or continuously, but are not limited thereto.

In the present disclosure, during the culture of the strain, pH of the culture may be adjusted by adding compounds such as ammonium hydroxide, potassium hydroxide, ammonia, phosphoric acid, and sulfuric acid to the culture in a proper manner. During the culture, foaming may be suppressed by using an antifoaming agent such as fatty acid polyglycol ester. Further, oxygen or oxygen-containing gas may be injected into the culture in order to maintain the aerobic state of the medium, or gas may not be injected or nitrogen, hydrogen, or carbon dioxide gas may be injected in order to maintain the anaerobic and microaerobic states.

The culture temperature may be maintained at 25° C. to 40° C., more specifically, at 28° C. to 37° C., but is not limited thereto. The culturing may be continued until a desired amount of a product is obtained, specifically, for 1 hour to 100 hours, but is not limited thereto.

The method of producing glutathione may further include an additional process, after the culturing step. The additional process may be appropriately selected according to the use of glutathione.

Specifically, the method of producing glutathione may include the step of collecting glutathione which is accumulated in the cells by the culturing step, for example, the step of collecting glutathione from one or more materials selected from the strain, a dry product, extract, culture, and lysate thereof, after the culturing step.

The method may further include the step of lysing the strain before or simultaneously with the collecting step. Lysis of the strain may be performed by a method commonly used in the art to which the present disclosure pertains, for example, a lysis buffer solution, a sonicator, heat treatment and French press, etc. In addition, the lysis step may include, but is not limited to, enzyme reactions such as cell wall degrading enzymes, nucleic acid degrading enzymes, nucleic acid transferases, and protein degrading enzymes.

With respect to the objects of the present disclosure, a dry yeast, yeast extract, yeast extract mix powder, or pure glutathione having a high content of glutathione may be prepared through the method of preparing glutathione, but are not limited thereto, and may be appropriately prepared according to the desired product.

As used herein, the "dry yeast" may be used interchangeably with the term "dry strain", etc. The dry yeast may be prepared by drying the yeast strain in which glutathione is accumulated, and specifically, may be included in a feed composition, a food composition, etc., but is not limited thereto.

As used herein, the term "yeast extract" may be used interchangeably with the term "strain extract", etc. The strain extract may refer to a material which remains after the cell wall is separated from the cell body of the strain. Specifically, the strain extract may refer to remaining components, excluding the cell wall, obtained by lysis of the cell body. The strain extract may include glutathione and may include, as components other than glutathione, one or more components of proteins, carbohydrates, nucleic acids, and fibers, but are not limited thereto.

The collecting step may be performed using an appropriate method known in the art, thereby collecting glutathione, which is the desired material.

The collecting step may include a purification process. The purification process may be a process of separating only pure glutathione from the strain. Through the purification process, pure glutathione may be prepared.

As needed, the method of preparing glutathione may further include the step of mixing an excipient with a material selected from the strain obtained after the step of culturing, the dry product, extract, culture, and lysate thereof, and glutathione collected therefrom. Through this mixing step, a yeast extract mix powder may be prepared.

The excipient may be appropriately selected for use according to the intended use or form thereof, and may be, for example, selected from starch, glucose, cellulose, lactose, glycogen, D-mannitol, sorbitol, lactitol, maltodextrin, calcium carbonate, synthetic aluminum silicate, calcium monohydrogen phosphate, calcium sulfate, sodium chloride, sodium hydrogen carbonate, purified lanolin, dextrin, sodium alginate, methylcellulose, colloidal silica gel, hydroxypropyl starch, hydroxypropylmethylcellulose, propylene glycol, casein, calcium lactate, primogel, gum arabic, and specifically, one or more components selected from starch, glucose, cellulose, lactose, dextrin, glycogen, D-mannitol, and maltodextrin, but is not limited thereto.

The excipient may include, for example, a preservative, a wetting agent, a dispersing agent, a suspending agent, a buffering agent, a stabilizing agent, or an isotonic agent, etc., but is not limited thereto.

Still another aspect of the present disclosure provides use of the variant of the present disclosure in the production of glutathione.

Still another aspect of the present disclosure provides use of the microorganism including the glutamate-cysteine ligase variant of the present disclosure in the production of glutathione.

The variant, polynucleotide, and microorganism are as described above.

Hereinafter, the present invention will be described in more detail with reference to Examples and Experimental Example. However, these Examples and Experimental Example are only for illustrating the present disclosure, and the scope of the present disclosure is not intended to be limited by these Examples and Experimental Example.

Example 1: Selection and Improvement of Glutathione-Producing Strain

Example 1-1: Selection of Glutathione-Producing Strain

Strains were obtained from nuruk containing various strains, and strains having glutathione-producing ability were selected by improving the strains.

In detail, grain samples, such as rice, barley, mung beans, oats, etc., were collected from a total of 20 regions, including Yongin, Icheon, Pyeongtaek, Hwaseong, Gyeonggi Province, Republic of Korea, and then ground, kneaded, wrapped in cloth, pressed tightly, wrapped in straw, followed by fermentation for 10 days. Thereafter, the samples were slowly dried to prepare nuruk.

In order to isolate various strains from the prepared nuruk, experiments were conducted as follows. 45 ml of saline was added to 5 g of nuruk and pulverized with a mixer. For pure separation of yeast strains, serial dilution was performed, followed by spreading on YPD Agar (10 g/L of Yeast extract, 20 g/L of Bacto peptone, 20 g/L of Glucose, based on 1 liter of distilled water) and incubation at 30° C. for 48 hours. Then, yeast colonies were streaked on YPD agar through colony morphology and microscopic inspection. 25 ml of YPD broth was dispensed into a 250 ml Erlenmeyer flask, the pure separated strain was seeded, and cultured with shaking (30° C., 200 rpm) for 48 hours to confirm glutathione production, and strain screening was performed.

For the improvement of the primarily isolated strains, random mutations were induced in the isolated strains. In detail, among the yeasts isolated from nuruk, a strain in which glutathione production was confirmed was isolated and named CJ-37 strain. The CJ-37 strain was cultured on a solid medium, seeded into a broth to obtain a culture medium, and the cells were irradiated with UV using a UV lamp. Thereafter, the UV-irradiated culture medium was plated on a plate medium to obtain only mutant strains forming colonies, and their glutathione production was examined.

As a result, from the mutant strains, the strain showing the highest glutathione production was selected as the glutathione-producing strain, and named CJ-5 strain, and deposited at the Korean Culture Center of Microorganisms (KCCM), an international depository authority under the Budapest Treaty, on Jul. 31, 2019, and assigned Accession No. KCCM12568P.

Example 1-2: Experiment for Additional Improvement to Increase Glutathione-Producing Ability In order to further improve the glutathione-producing ability of the CJ-5 strain, mutations were induced as follows.

The CJ-5 strain was cultured on a solid medium, seeded into a broth to obtain a culture medium, and the cells were irradiated with UV using a UV lamp. Thereafter, the UV-irradiated culture medium was plated on a plate medium to obtain only mutant strains forming colonies, and the strain showing the most improved glutathione-producing ability was isolated and named CC02-2490 strain, and deposited at the Korean Culture Center of Microorganisms (KCCM), an international depository authority under the Budapest Treaty, on Jan. 17, 2020, and assigned Accession No. KCCM12659P.

As a result of analyzing a nucleotide sequence of the glutathione biosynthetic gene gsh1 in relation to the increase in the glutathione-producing ability of the CC02-2490 strain, it was confirmed that cysteine which is an 86$^{th}$ amino acid of the GSH1 protein (SEQ ID NO: 1) encoded by the gsh1 gene was replaced by arginine.

Example 1-3: Experiment for Additional Improvement to Increase Glutathione-Producing Ability In order to further improve the glutathione-producing ability of the 0002-2490 strain, mutations were induced as follows.

The 0002-2490 strain was cultured on a solid medium, seeded into a broth to obtain a culture medium, and the cells were irradiated with UV using a UV lamp. Thereafter, the UV-irradiated culture medium was plated on a plate medium to obtain only mutant strains forming colonies, and the strain showing the most improved glutathione-producing ability was isolated and named 0002-2544 strain, and deposited at the Korean Culture Center of Microorganisms (KCCM), an international depository authority under the Budapest Treaty, on Feb. 20, 2020, and assigned Accession No. KCCM12674P.

As a result of analyzing a nucleotide sequence of the glutathione biosynthetic gene gsh1 in relation to the increase in the glutathione-producing ability of the CC02-2544 strain, it was confirmed that variations of −250(C→T), −252(G→A), −398(A→T), −399(A→C), −407(T→C), −409(T→C) upstream of GSH1 ORF occurred (SEQ ID NO: 12).

Example 2: Experiment for Additional Improvement of CC02-2544 Strain to Increase Glutathione-Producing Ability In order to further improve the glutathione-producing ability of the 0002-2544 strain, mutations were induced as follows.

The 0002-2544 strain was cultured on a solid medium, seeded into a broth to obtain a culture medium, and the cells were irradiated with UV using a UV lamp. Thereafter, the UV-irradiated culture medium was plated on a plate medium to obtain only mutant strains forming colonies, followed by nucleotide sequence analysis.

As a result of the experiment, it was confirmed that methionine was substituted for the 653$^{rd}$ amino acid (glycine) of GSH1, which is a protein encoded by the glutathione biosynthetic gene gsh1 of the strain showing 27% increase in the glutathione content. This strain was named 0002-2816 and deposited at the Korean Culture Center of Microorganisms (KCCM), an international depository authority under the Budapest Treaty, on Dec. 8, 2020, and assigned Accession No. KCCM12891P.

Example 3: Experiment of GSH1 G653 Residue Variation

From the above results of Example 2, it was determined that position 653 of the GSH1 protein would be important for glutathione production, and strain variants of *Saccharomyces cerevisiae* (*S. cerevisiae*) CEN.PK2-1 D and CC02-2544 strain were prepared to express protein variants in which the amino acid at position 653 of the GSH1 protein was substituted with another amino acid, and it was intended to examine whether or not the glutathione production was increased. On the other hand, as mentioned above, the CC02-2544 strain is a strain having variations of −250 (C→T), −252(G→A), −398(A→T), −399(A→C), −407 (T→C), −409(T→C) upstream of GSH1 ORF in the GSH1 C86R strain variant. In the corresponding strain, a variation of the amino acid at position 653 of the GSH1 protein was additionally introduced.

To prepare a strain in which the amino acid at position 653 of GSH1 protein of yeast *Saccharomyces cerevisiae* was substituted with methionine, pWAL100 and pWBR100 plasmids were used with reference to the contents disclosed in a literature, Lee T H, et al. (J. Microbiol. Biotechnol. (2006), 16(6), 979-982). In detail, PCR was performed as follows using the genomic DNA of the CJ-5 strain as a template. PCR was performed using primers of SEQ ID NO: 4 and SEQ ID NO: 5 to obtain a part of GSH1 N-terminal sequence including the N-terminal BamHI flanking sequence, the GSH1 ORF start codon, and the G653M variation-coding sequence, and using primers of ID NO: 6 and SEQ ID NO: 7 to obtain a part of the GSH1 C-terminal sequence including the C-terminal XhoI flanking sequence, the GSH1 ORF stop codon, and the G653M variation-coding sequence. Subsequently, overlap PCR was performed using these two sequences as templates and SEQ ID NO: 4 and SEQ ID NO: 7, and as a result, a GSH1 ORF fragment including the GSH1 protein variant-coding sequence in which the amino acid at position 653 was substituted with methionine, the N-terminal BamHI, and the C-terminal XhoI restriction enzyme sequence. The ORF fragment was treated with BamHI and XhoI and then cloned into pWAL100 vector which had been treated with the same enzymes to prepare a pWAL100-GSH1(G653M) vector.

Further, PCR was performed using the genomic DNA of the CJ-5 strain as a template and SEQ ID NO: 8 and SEQ ID NO: 9 to obtain a fragment of 500 bp after the GSH1 ORF stop codon containing the N-terminal SpeI and C-terminal NcoI restriction enzyme sequences. Then, the fragment was cloned into pWBR100 which had been treated with the same restriction enzymes to prepare a pWBR100-GSH1 vector.

Finally, to prepare a DNA fragment to be introduced into yeast, a PCR product containing the methionine variation-coding sequence and a part of KIURA3 was obtained using the previously prepared pWAL100-GSH1 (G653M) vector as a template and primers of SEQ ID NO: 4 and SEQ ID NO: 10, and a PCR product containing a part of KIURA3 and 500 bp after the GSH1 stop codon was obtained using the pWBR100-GSH1 vector as a template and primers of SEQ ID NO: 11 and SEQ ID NO: 9, and then each PCR product was transformed into *S. cerevisiae* CEN.PK2-1D and *S. cerevisiae* CC02-2544 at the same molar ratio. PCR was performed under conditions of heat denaturation at 95° C. for 5 minutes, annealing at 53° C. for 1 minute, and polymerization at 72° C. for 1 minute per 1 kb. Yeast transformation was performed using a lithium acetate method modified from Geitz's thesis (Nucleic Acid Research, 20(6), 1425). In detail, yeast cells at O.D. of 0.7~1.2 were washed twice with lithium acetate/TE buffer, and then the PCR products and single stranded DNA (Sigma D-7656) were mixed together and incubated in lithium acetate/TE/40% PEG buffer for 30 minutes at 30° C. and 42° C. for 15 minutes, and then the cells were cultured on a SC (2% glucose) agar plate without uracil until colonies were visible, and a strain in which the GSH1 G653M variation-coding sequence and the KIURA3 gene were introduced was obtained. Then, in order to remove KIURA3, each strain was incubated overnight in 2 ml of YPD, diluted 1/100, and spread on an SC (2% glucose) agar plate containing 0.1% 5-FOA to prepare *S. cerevisiae* CEN.PK2-1D GSH1 G653M strain variant and *S. cerevisiae* 0002-2544 GSH1 G653M strain variant from which the uracil marker was removed. A strain capable of expressing the GSH1 protein variant in which other types of amino acids than methionine were substituted was also prepared in the same manner, except for using a pair of primers in which the sequence encoding methionine at position 653 on the primer sequences of SEQ ID NO: 5 and SEQ ID NO: 6 was substituted with a sequence encoding another amino acid.

TABLE 1

| Primer | 5' -> 3' sequence |
|---|---|
| F_BamHI_GSH1(SEQ ID NO: 4) | GGTAGGATCCATGGGACTCTTAGCTTTGGGCAC |
| R_GSH1_G653M(SEQ ID NO: 5) | GTCAATTCCATTTTTGAATCGTCCA |
| F_GSH1_G653M(SEQ ID NO: 6) | ATTCAAAAATGGAATTGACATCCTT |
| R_Xhol_GSH1(SEQ ID NO: 7) | ATGACTCGAGTTAACATTTGCTTTCTATTGAAGGC |
| F_Spel_GSH1_DW(SEQ ID NO: 8) | TAGAACTAGTACTCCTTTTATTTCGGTTGTGAA |
| R_Ncol_GSH1_DW(SEQ ID NO: 9) | GCTGCCATGGGAATAGTGTGAACCGATAACTGTGT |
| R_AL killer(SEQ ID NO: 10) | GAGCAATGAACCCAATAACGAAATCTT |
| F_BR killer(SEQ ID NO: 11) | CTTGACGTTCGTTCGACTGATGAG |

The results of measuring the concentration and content of glutathione (GSH) produced by culturing each of the prepared strains for 26 hours are shown in Table 2 and Table 3. The GSH1 G653M variation (SEQ ID NO: 13) was additionally introduced into the 0002-2544 strain. As a result, the GSH concentration increased by 77 mg/L from 471.5 mg/L to 548.5 mg/L, and as a result of introducing the GSH1 G653M variation (SEQ ID NO: 3) into the CEN.PK-1D strain, the GSH concentration increased by 58 mg/L from 42 mg/L to 100 mg/L.

Example 3-1: Introduction of GSH1 G653 Variation into CC02-2544 Strain

TABLE 2

| | | S. cerevisiae CC02-2544 | | |
|---|---|---|---|---|
| | GSH concentration (mg/L) | GSH content (%) | GSH concentration relative to control (fold) | GSH content relative to control (fold) |
| WT (wild-type) | 471.5 | 3.2 | 1.00 | 1.00 |
| GSH1 G653M | 548.5 | 3.8 | 1.16 | 1.19 |
| GSH1 G653N | 507.0 | 3.3 | 1.08 | 1.03 |
| GSH1 G653C | 440.5 | 3.2 | 0.93 | 1.00 |
| GSH1 G653A | 454.6 | 3.2 | 0.96 | 1.00 |
| GSH1 G653L | 471.5 | 3.2 | 1.00 | 1.00 |
| GSH1 G653T | 445.5 | 3.0 | 0.94 | 0.94 |
| GSH1 G653H | 443.7 | 3.0 | 0.94 | 0.93 |
| GSH1 G653P | 391.3 | 2.9 | 0.83 | 0.90 |
| GSH1 G653V | 346.5 | 2.4 | 0.73 | 0.75 |

Example 3-2: Introduction of GSH1 G653 Variation into CEN.PK-1D Strain

TABLE 3

| | | S. cerevisiae CEN.PK2-1D | | |
|---|---|---|---|---|
| | GSH concentration (mg/L) | GSH content (%) | GSH concentration relative to control (fold) | GSH relative to control (fold) |
| WT (wild-type) | 42.0 | 0.4 | 1.00 | 1.00 |
| GSH1 G653M | 100.0 | 0.9 | 2.38 | 2.37 |
| GSH1 G653L | 53.0 | 0.5 | 1.26 | 1.27 |
| GSH1 G653A | 40.0 | 0.4 | 0.95 | 1.02 |
| GSH1 G653C | 42.0 | 0.4 | 1.00 | 1.02 |
| GSH1 G653N | 45.0 | 0.4 | 1.07 | 1.02 |

TABLE 3-continued

| | | S. cerevisiae CEN.PK2-1D | | |
|---|---|---|---|---|
| | GSH concentration (mg/L) | GSH content (%) | GSH concentration relative to control (fold) | GSH relative to control (fold) |
| GSH1 G653H | 39.0 | 0.4 | 0.95 | 0.96 |
| GSH1 G653T | 37.0 | 0.4 | 0.89 | 0.94 |
| GSH1 G653V | 36.0 | 0.3 | 0.86 | 0.87 |
| GSH1 G653P | 18.0 | 0.2 | 0.43 | 0.51 |

From this, it can be seen that the GSH1 variant, in which glycine at position 653 of the GSH1 protein was substituted with methionine, greatly increases the glutathione-producing ability.

This confirmed that the novel GSH1 variant developed in this disclosure exhibits the increase in the glutathione production. In addition, the yeast showing high production of glutathione by including the GSH1 variant of the present disclosure, a dry product thereof, an extract thereof, a culture thereof, a lysate thereof, and produced glutathione have antioxidant effects, detoxification effects, and immunity-enhancing effects, and thus they may also be usefully used in cosmetic compositions, food compositions, feed compositions, pharmaceutical compositions, and preparation thereof.

Reference Example: Experiment of Substitution of C86 Residue of GSH1 Protein

Strain variants of Saccharomyces cerevisiae (S. cerevisiae) CEN.PK2-1 D and Saccharomyces cerevisiae (S. cerevisiae) CJ-5 strain were prepared to express a protein variant in which the cysteine amino acid at position 86 of the GSH1 protein was substituted with another amino acid. It was intended to examine whether glutathione production increased.

To prepare a strain in which cysteine at position 86 of GSH1 protein of Saccharomyces cerevisiae was substituted with arginine, pWAL100 and pWBR100 plasmids were used with reference to the contents disclosed in a literature, Lee T H, et al. (J. Microbiol. Biotechnol. (2006), 16(6), 979-982). In detail, PCR was performed as follows using the genomic DNA of the CJ-5 strain as a template. PCR was performed using primers of SEQ ID NO: 4 and SEQ ID NO: 14 to obtain a part of GSH1 N-terminal sequence including the N-terminal BamHI flanking sequence, the GSH1 ORF start codon, and the C86R variation-coding sequence, and using primers of ID NO: 15 and SEQ ID NO: 7 to obtain a part of the GSH1 C-terminal sequence including the C-terminal XhoI flanking sequence, the GSH1 ORF stop codon, and the C86R variation-coding sequence. Subsequently, overlap PCR was performed using these two sequences as templates and SEQ ID NO: 4 and SEQ ID NO: 7, and as a result, a GSH1 ORF fragment including the GSH1 protein variant-coding sequence in which cysteine at position 86 was substituted with arginine, the N-terminal BamHI, and the C-terminal XhoI restriction enzyme sequence. The ORF fragment was treated with BamHI and XhoI and then cloned into pWAL100 vector which had been treated with the same enzymes to prepare a pWAL100-GSH1(C86R) vector.

Further, PCR was performed using the genomic DNA of the CJ-5 strain as a template and SEQ ID NO: 8 and SEQ ID NO: 9 to obtain a fragment of 500 bp after the GSH1 ORF stop codon containing the N-terminal SpeI and C-terminal NcoI restriction enzyme sequences, which was then treated with SpeI and NcoI restriction enzymes. Then, the fragment was cloned into pWBR100 which had been treated with the same restriction enzymes to prepare a pWBR100-GSH1 vector.

Finally, to prepare a DNA fragment to be introduced into yeast, a PCR product containing the arginine variation-coding sequence and a part of KlURA3 was obtained using the previously prepared pWAL100-GSH1(C86R) vector as a template and primers of SEQ ID NO: 4 and SEQ ID NO: 10, and a PCR product containing a part of KlURA3 and 500 bp after the GSH1 stop codon was obtained using the pWBR100-GSH1 vector as a template and primers of SEQ ID NO: 11 and SEQ ID NO: 9, and then each PCR product was transformed into *S. cerevisiae* CEN.PK2-1 D and *S. cerevisiae* CJ-5 at the same molar ratio. PCR was performed under conditions of heat denaturation at 95° C. for 5 minutes, annealing at 53° C. for 1 minute, and polymerization at 72° C. for 1 minute per 1 kb. Yeast transformation was performed using a lithium acetate method modified from Geitz's thesis (Nucleic Acid Research, 20(6), 1425). In detail, yeast cells at O.D. of 0.7 to 1.2 were washed twice with lithium acetate/TE buffer, and then the PCR products and single stranded DNA (Sigma D-7656) were mixed together and incubated in lithium acetate/TE/40% PEG buffer for 30 minutes at 30° C. and 42° C. for 15 minutes, and then the cells were subjected to stationary culture on a SC (2% glucose) agar plate without uracil until colonies were visible, and a strain in which the GSH1 C86R variation-coding sequence and the KlURA3 gene were introduced was obtained. Then, in order to remove KlURA3, each strain was incubated overnight in 2 ml of YPD, diluted 1/100, and spread on an SC (2% glucose) agar plate containing 0.1% 5-FOA to prepare *S. cerevisiae* CEN.PK2-1D GSH1 C86R strain variant and *S. cerevisiae* CJ-5 GSH1 C86R strain variant from which the uracil marker was removed. A strain capable of expressing the GSH1 protein variant in which other types of amino acids than arginine were substituted was also prepared in the same manner, except for using a pair of primers in which the sequence encoding arginine at position 86 on the primer sequences of SEQ ID NO: 14 and SEQ ID NO: 15 was substituted with a sequence encoding another amino acid.

TABLE 4

| Primer | 5'→3' sequence |
|---|---|
| F_BamHI_GSH1(SEQ ID NO: 4) | GGTAGGATCCATGGGACTCTTAGCTTTGGGCAC |
| R_GSH1_C86R(SEQ ID NO: 14) | TTAGCCTCCCTAAGGGACGAATCCT |
| F_GSH1_C86R(SEQ ID NO: 15) | CGTCCCTTAGGGAGGCTAACGATGT |
| R_XhoI_GSH1(SEQ ID NO: 7) | ATGACTCGAGTTAACATTTGCTTTCTATTGAAGGC |
| F_SpeI_GSH1_DW(SEQ ID NO: 8) | TAGAACTAGTACTCCTTTTATTTCGGTTGTGAA |
| R_NcoI_GSH1_DW(SEQ ID NO: 9) | GCTGCCATGGGAATAGTGTGAACCGATAACTGTGT |
| R_AL killer(SEQ ID NO: 10) | GAGCAATGAACCCAATAACGAAATCTT |
| F_BR killer(SEQ ID NO: 11) | CTTGACGTTCGTTCGACTGATGAG |

The results of measuring the concentration of glutathione (GSH) produced by culturing each of the prepared strains for 26 hours are shown in Table 5 and Table 6.

TABLE 5

| | S. cerevisiae CEN.PK2-1D | |
|---|---|---|
| | GSH concentration (mg/L) | |
| Mutant | 26 hr | Increase (fold) |
| WT | 86.0 | 1.00 |
| F | 109.5 | 1.27 |
| H | 103.2 | 1.20 |
| K | 100.7 | 1.17 |
| E | 100.1 | 1.16 |
| G | 99.5 | 1.16 |
| D | 97.5 | 1.13 |
| N | 96.3 | 1.12 |
| R | 95.2 | 1.11 |
| Y | 94.6 | 1.10 |
| I | 93.0 | 1.08 |
| L | 92.2 | 1.07 |
| P | 92.0 | 1.07 |
| W | 90.8 | 1.06 |
| Q | 90.3 | 1.05 |
| S | 90.0 | 1.05 |
| M | 89.9 | 1.05 |
| T | 86.6 | 1.01 |
| A | 86.4 | 1.00 |
| V | 86.2 | 1.00 |

TABLE 6

| | S. cerevisiae CJ-5 | |
|---|---|---|
| | GSH concentration (mg/L) | |
| Mutant | 26 hr | Increase (fold) |
| WT | 271.3 | 1.00 |
| R | 330.0 | 1.22 |
| N | 321.9 | 1.19 |
| D | 318.4 | 1.17 |
| E | 314.4 | 1.16 |
| P | 304.2 | 1.12 |
| K | 302.4 | 1.11 |
| A | 294.9 | 1.09 |
| Q | 286.4 | 1.06 |
| V | 285.6 | 1.05 |
| F | 282.5 | 1.04 |

TABLE 6-continued

| | S. cerevisiae CJ-5 | |
|---|---|---|
| | GSH concentration (mg/L) | |
| Mutant | 26 hr | Increase (fold) |
| Y | 277.5 | 1.02 |
| W | 276.0 | 1.02 |
| S | 274.5 | 1.01 |
| T | 273.9 | 1.01 |
| I | 273.5 | 1.01 |
| H | 272.1 | 1.00 |
| G | 272.0 | 1.00 |

As a result of the experiment, it was confirmed that when cysteine at position 86 of the GSH1 protein was substituted with another amino acid, the glutathione-producing ability was increased, as compared to those of including the wild-type GSH1 protein.

This indicates that the GSH1 variant in which cysteine at position 86 of the GSH1 protein is substituted with another amino acid greatly increases the glutathione-producing ability.

Based on the above description, it will be understood by those skilled in the art that the present disclosure may be implemented in a different specific form without changing the technical spirit or essential characteristics thereof. In this regard, it should be understood that the above embodiment is not limitative, but illustrative in all aspects. The scope of the disclosure is defined by the appended claims rather than by the description preceding them, and therefore all changes and modifications that fall within metes and bounds of the claims, or equivalents of such metes and bounds are therefore intended to be embraced by the claims.

Effect of the Invention

A novel glutamate-cysteine ligase variant of the present disclosure greatly increases glutathione production, and thus it may be usefully applied to high production of glutathione. As described, yeast showing high production of glutathione, a dry product thereof, an extract thereof, a culture thereof, a lysate thereof, and produced glutathione have antioxidant effects, detoxification effects, and immunity-enhancing effects, and thus they may also be usefully used in cosmetic compositions, food compositions, feed compositions, pharmaceutical compositions, and preparation thereof.

What is claimed is:

1. A glutamate-cysteine ligase variant comprising a sequence having at least 80% sequence identity to SEQ ID NO: 1, wherein the amino acid corresponding to position 653 of SEQ ID NO: 1 is substituted with methionine.

2. The glutamate-cysteine ligase variant of claim 1, wherein the amino acid corresponding to position 653 is glycine.

3. The glutamate-cysteine ligase variant of claim 1, wherein the glutamate-cysteine ligase variant comprises SEQ ID NO: 3.

4. The glutamate-cysteine ligase variant of claim 1, wherein the glutamate-cysteine ligase variant has an additional substitution of an amino acid corresponding to position 86 with another amino acid.

5. The glutamate-cysteine ligase variant of claim 4, wherein the glutamate-cysteine ligase variant comprises SEQ ID NO: 13.

6. A polynucleotide encoding the glutamate-cysteine ligase variant of claim 1.

7. A vector comprising the polynucleotide of claim 6.

8. A microorganism producing glutathione, the microorganism comprising one or more selected from the group consisting of: the glutamate-cysteine ligase variant of claim 1; a polynucleotide encoding the glutamate-cysteine ligase variant of claim 1; and a vector comprising the polynucleotide encoding the glutamate-cysteine ligase variant of claim 1.

9. The microorganism producing glutathione of claim 8, wherein the microorganism is a microorganism of the genus *Saccharomyces*.

10. The microorganism producing glutathione of claim 8, wherein the microorganism is *Saccharomyces cerevisiae*.

11. A method of producing glutathione, the method comprising the step of culturing, in a culture medium, a microorganism comprising one or more selected from the group consisting of:

the glutamate-cysteine ligase variant of claim 1; a polynucleotide encoding the glutamate-cysteine ligase variant of claim 1; and a vector comprising the polynucleotide encoding the glutamate-cysteine ligase variant of claim 1, wherein the microorganism produces glutathione.

12. The method of claim 11, further comprising the step of collecting the glutathione.

13. The glutamate-cysteine ligase variant of claim 1, wherein the glutamate-cysteine ligase variant comprises a sequence having at least 90% sequence identity to SEQ ID NO: 1.

14. The glutamate-cysteine ligase variant of claim 1, wherein the glutamate-cysteine ligase variant comprises a sequence having at least 99% sequence identity to SEQ ID NO: 1.

15. The glutamate-cysteine ligase variant of claim 1, wherein the glutamate-cysteine ligase variant comprises a sequence having at least 90% sequence identity to SEQ ID NO: 3.

16. The glutamate-cysteine ligase variant of claim 1, wherein the glutamate-cysteine ligase variant comprises a sequence having at least 99% sequence identity to SEQ ID NO: 3.

17. The glutamate-cysteine ligase variant of claim 1, wherein the glutamate-cysteine ligase variant comprises a sequence having at least 99% sequence identity to SEQ ID NO: 13.

18. A method of producing glutathione, the method comprising the step of culturing, in a culture medium, a microorganism comprising one or more selected from the group consisting of:

the glutamate-cysteine ligase variant of claim 3; a polynucleotide encoding the glutamate-cysteine ligase variant of claim 3; and a vector comprising the polynucleotide encoding the glutamate-cysteine ligase variant of claim 3, wherein the microorganism produces glutathione.

19. A method of producing glutathione, the method comprising the step of culturing, in a culture medium, a microorganism comprising one or more selected from the group consisting of:

the glutamate-cysteine ligase variant of claim 4; a polynucleotide encoding the glutamate-cysteine ligase variant of claim 4; and a vector comprising the polynucleotide encoding the glutamate-cysteine ligase variant of claim 4, wherein the microorganism produces glutathione.

20. A method of producing glutathione, the method comprising the step of culturing, in a culture medium, a microorganism comprising one or more selected from the group consisting of:

the glutamate-cysteine ligase variant of claim 5; a polynucleotide encoding the glutamate-cysteine ligase variant of claim 5; and a vector comprising the polynucleotide encoding the glutamate-cysteine ligase variant of claim 5, wherein the microorganism produces glutathione.

* * * * *